(12) United States Patent
Stayton et al.

(10) Patent No.: US 7,625,764 B2
(45) Date of Patent: Dec. 1, 2009

(54) STIMULI-RESPONSIVE POLYMER DEVICES

(75) Inventors: Patrick S. Stayton, Seattle, WA (US); Allan S. Hoffman, Seattle, WA (US); Noah Malmstadt, Pasadena, CA (US); Tsuyoshi Shimoboji, Shizuoka (JP); Samarth Kulkarni, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 11/197,771

(22) Filed: Aug. 3, 2005

(65) Prior Publication Data

US 2006/0127925 A1 Jun. 15, 2006

Related U.S. Application Data

(63) Continuation of application No. PCT/US2004/003845, filed on Feb. 11, 2004.

(60) Provisional application No. 60/447,041, filed on Feb. 11, 2003.

(51) Int. Cl.
*C12M 1/34* (2006.01)
*C12M 3/00* (2006.01)
*G01N 33/543* (2006.01)

(52) U.S. Cl. .............. 436/518; 435/7.1; 435/283.1; 435/287.1; 435/288.3; 435/288.7; 436/528; 436/532; 422/50; 422/55; 422/61; 422/68.1; 422/82.05

(58) Field of Classification Search ............... 435/7.1, 435/283.1, 287.1, 288.3, 288.7; 436/518, 436/528, 532; 422/50, 55, 61, 68.1, 82.05
See application file for complete search history.

(56) References Cited

U.S. PATENT DOCUMENTS

| | | | | |
|---|---|---|---|---|
| 4,780,409 A | * | 10/1988 | Monji et al. | ............... 435/7.36 |
| 5,135,876 A | | 8/1992 | Andrade et al. | |
| 5,378,608 A | * | 1/1995 | Marui et al. | ................. 435/7.5 |
| 5,451,411 A | | 9/1995 | Gombotz et al. | |
| 5,466,348 A | | 11/1995 | Holm-Kennedy | |
| 5,569,364 A | | 10/1996 | Hooper et al. | |
| 5,770,627 A | | 6/1998 | Inoue et al. | |
| 5,827,743 A | * | 10/1998 | Tanzawa | ..................... 435/430 |
| 5,997,961 A | * | 12/1999 | Feng et al. | .................. 427/515 |
| 5,998,588 A | | 12/1999 | Hoffman et al. | |

(Continued)

FOREIGN PATENT DOCUMENTS

EP  1281436 A1  2/2003

(Continued)

OTHER PUBLICATIONS

Akiyoshi, K., et al., "Controlled Association of Amphiphilic Polymers in Water: Thermosensitive Nanoparticles Formed by Self-Assembly of Hydrophobically Modified Pullulans and Poly(N-isopropylacrylamides)," Macromolecules 33(9):3244-3249, Apr. 6, 2000.

(Continued)

*Primary Examiner*—Melanie J. Yu
(74) *Attorney, Agent, or Firm*—Christensen O'Connor Johnson Kindness PLLC

(57) ABSTRACT

Conjugates that include polymers that are reversibly self-associative in response to a stimulus and methods for using the conjugates.

12 Claims, 13 Drawing Sheets

U.S. PATENT DOCUMENTS

| | | | |
|---|---|---|---|
| 6,165,509 | A | 12/2000 | Hoffman et al. |
| 6,355,163 | B2* | 3/2002 | Hindsgaul et al. ........ 210/198.2 |
| 6,447,764 | B1* | 9/2002 | Bayer et al. ................ 424/78.1 |
| 6,486,213 | B1 | 11/2002 | Chen et al. |
| 6,641,735 | B1* | 11/2003 | Yoshizako et al. .......... 210/635 |
| 6,740,409 | B1* | 5/2004 | Granick et al. ............ 428/411.1 |
| 6,835,393 | B2 | 12/2004 | Hoffman et al. |
| 2003/0218130 | A1* | 11/2003 | Boschetti et al. ............ 250/288 |
| 2004/0077024 | A1* | 4/2004 | Holmberg ................... 435/7.5 |

FOREIGN PATENT DOCUMENTS

| | | |
|---|---|---|
| WO | WO 01/51092 A2 | 7/2001 |
| WO | 0216571 A1 | 2/2002 |

OTHER PUBLICATIONS

Buchholz, B.A., et al., "Microchannel DNA Sequencing Matrices With Switchable Viscosities," Electrophoresis 23(10):1398-1409, May 2002.

Hoffman, A.S., et al., "Really Smart Bioconjugates of Smart Polymers and Receptor Proteins" Journal of Biomedical Materials Research 52(4):577-586, Dec. 15, 2000.

Kanazawa, H., and Y. Matsushima, "Temperature-Responsive Chromatography," Trends in Analytical Chemistry 17(7):435-440, Aug. 1998.

Kondo, A., et al., "Development and Application of Thermo-Sensitive Magnetic Immunomicrospheres for Antibody Purification," Applied Microbiology and Biotechnology 41:99-105, 1994.

Kulkarni, S., et al., "Reversible Meso-Scale Smart Polymer-Protein Particles of Controlled Sizes," Bioconjugate Chemistry 15(4):747-753, Jun. 30, 2004.

Malmstadt, N., et al., "A Smart Microfluidic Affinity Chromatography Matrix Composed of Poly(N-isopropylacrylamide)-Coated Beads," Analytical Chemistry 75(13):2943-2949, Jun. 3, 2003.

Malmstadt, N., et al., "'Smart' Mobile Affinity Matrix for Microfluidic Immunoassays," Lab on a Chip 4(4):412-415, Apr. 6, 2004.

Matsubara, C., et al., "Determination of Trace Amounts of Phosphate in Water After Preconcentration Using a Thermally Reversible Polymer," Analyst 118(5):553-556, May 1993.

Miura, M., et al., "Application of LCST Polymer-Cell Receptor Conjugates for Cell Culture on Hydrophobic Surfaces," The 17th Annual Meeting of the Society for Biomaterials, Scottsdale, Arizona, May 1-5, 1991, p. 130.

Monji, N., and A.S. Hoffman, "A Novel Immunoassay System and Bioseparation Process Based on Thermal Phase Separating Polymers," Applied Biochemistry and Biotechnology 14:107-120, Mar. 1987.

Monji, N., et al., "Application of a Thermally-Reversible Polymer-Antibody Conjugate in a Novel Membrane-Based Immunoassay," Biochemical and Biophysical Research Communications 172(2):652-660, Oct. 30, 1990.

Tang, Z., et al., "Single Nucleotide Polymorphisms (SNPs) Assay Using Reversible Association and Dispersion of DNA-Linked Colloidal Nanoparticles," Nucleic Acids Research Supplement 1(1):165-166, 2001.

Yoshizako, K., and Y. Akiyama, "Regulation of Protein Binding Toward a Ligand on Chromatographic Matrixes by Masking and Forced-Releasing Effects Using Thermoresponsive Polymer," Analytical Chemistry 74(16):4160-4166, Aug. 15, 2002.

* cited by examiner

STIMULI-RESPONSIVE POLYMER DEVICES

CROSS-REFERENCES TO RELATED APPLICATIONS

This application is a continuation of International Application No. PCT/US2004/003845, filed Feb. 11, 2004, which claims the benefit of U.S. Provisional Application No. 60/447,041, filed Feb. 11, 2003, each application is incorporated herein by reference in its entirety.

STATEMENT OF GOVERNMENT LICENSE RIGHTS

This invention was made with government support under Government Contract No. 5 RO1 GM53771-07, awarded by the National Institutes of Health. The government has certain rights in the invention.

FIELD OF THE INVENTION

The present invention relates to stimuli-responsive polymer conjugates and methods for using the conjugates.

BACKGROUND OF THE INVENTION

There is a strong need for rapid and simplified upstream processing of complex samples for (bio)chemical analysis. This need is common to conventional laboratory and diagnostic assay systems, as well as to newer microdevice and microfluidic systems that offer simplified fluid handling, conservation of scarce samples and reagents, and portability.

The controlled separation and release of specific biological molecules from complex mixtures is a key process in most bioanalytical and diagnostic technologies. Efficient, specific bioseparation processes are necessary because of the stringent purity requirements for many bioanalytical and diagnostic technologies. Affinity bioseparation systems rely on a specific biological interaction between a target biomolecule and an affinity ligand. Affinity chromatography is the most commonly used affinity bioseparation technology that relies on the attachment of an affinity ligand to an immobile matrix. A complex mixture containing the target biomolecule is passed over this matrix, and the target molecule binds to its affinity ligand, allowing the other components of the mixture to be washed away. The separated target molecule is then eluted from the column, typically with a chemical eluent that weakens the affinity interaction. Affinity chromatography is very efficient and specific in purifying target biomolecules and cells.

Affinity separations typically rely on biomolecular recognition. The control of recognition steps is thus an integral aspect of bioprocessing steps that accompany bioanalytical and diagnostic technology. For many affinity separation, diagnostic, biosensor, biochip and bioprocessing technologies that utilize biomolecular recognition properties, there is a continuing need for better control routes. Many of the current methods are relatively harsh and can lead to damage of biomolecules and cells. In addition, the environmental signals are typically large general solution changes and thus not targeted to selective recognition components.

"Smart" polymers, which reversibly change their physical properties in response to small and controllable stimuli (e.g., changes in pH, temperature, and light), to control recognition events by acting as environmental antennae and switches. These smart polymers reversibly cycle between an extended and hydrophilic random coil, and a collapsed, hydrophobic state that is reduced in average volume by about 3-fold. The polymers serve as environmental sensors and differentially control access of ligands or substrates to binding or catalytic sites as a function of their expanded or collapsed states. This general approach targets mild environmental signals to specific polymer-protein conjugates, and thus, for example, allows differential control of different antibodies in a device by using conjugated polymers that are sensitive to different signals (e.g., antibody 1 with pH, antibody 2 with temperature, antibody 3 with light).

The following references describe various efforts to employ affinity recognition for the controlled separation and release of bioanalytical, therapeutic drug, or diagnostic agents. References implementing the smart polymers mentioned above are included.

U.S. Pat. No. 5,451,411 describes alginate beads designed to deliver cationic therapeutic agents to the luminal side of the small intestine via oral ingestion. Co-encapsulation of polyanionic additives with the therapeutic agent followed by acid treatment of the resulting bead enhances release of the agent. Sustained release of the agent is triggered within a nontoxic gastrointestinal pH range.

U.S. Pat. No. 5,770,627 describes hydrophobically-modified bioadhesive polyelectrolytes capable of sustained release of a pharmaceutically, cosmetically, or prophylactically acceptable agent. The hydrophobic component (a hydrophobic moiety or hydrophobic polymer) facilitates micelle formation, permitting delivery of the cationic or hydrophobic and/or anionic agent. Uptake of water by the bioadhesive polyelectrolyte portion (a carboxylic acid-containing polymer) results in swelling and "stickiness," thereby allowing the sustainable release of the agent.

U.S. Pat. No. 6,486,213 describes block and graft copolymers for use in the topical delivery of drugs. The copolymer is physically mixed with one or more drugs to form a copolymer-drug mixture. These copolymers contain a pH-sensitive polymer component, which swells and adheres to the treatment area upon uptake of water, and a temperature-sensitive polymer component, which facilitates controlled release of the drug.

U.S. Pat. No. 5,998,588 describes stimuli-responsive interactive molecular conjugates. The conjugates include a stimuli-responsive component that is an environmentally sensitive polymer and an interactive molecular component that can be a variety of ligand-binding biomolecules. In the conjugate, a stimuli-responsive polymer is coupled to an interactive biomolecule proximal to the ligand-binding site of the ligand-binding molecule such that, upon stimulation, the polymer alters ligand-biomolecule binding behavior. External stimuli, such as temperature, pH, or light cause the stimulus-responsive component to undergo a conformational or physico-chemical change that can lead to a structural transition in the conjugate itself, thereby modulating the activity of the interactive biomolecule.

U.S. Pat. No. 6,165,509 describes PEGylated drugs complexed with bioadhesive polymers (e.g., polyacrylic, polymethacrylic, polyethylacrylic acids, and chitosan). The PEGylated drug includes a polyethylene glycol covalently bonded to the drug. Upon uptake of water at the treatment site, the bioadhesive polymer becomes "sticky" and neutral pH exposure facilitates the dissociation of the PEGylated drug from the bioadhesive polymer. Sustained drug release is thereby achieved via topical administration.

WO 01/51092 describes a composition, for disruption of cell membrane, used for delivering diagnostic or therapeutic agents to cytoplasm of cells. The composition includes a conjugate having a hydrophobic component linked to a hydrophilic component by a linkage capable of being disrupted or degraded, preferably by a change in pH. The conjugate can further include a therapeutic, diagnostic, or prophylactic agent. The hydrophobic component (e.g., environmentally sensitive polymer) is membrane disruptive. The hydrophilic conjugate operates to first enhance membrane transport of the agent, to next undergo linkage degradation, and to finally release of the agent into the cytosol.

Despite the advances noted above, there still exists a need for improved methods of biomolecule capture and release. The present invention seeks to fulfill this need and provides further related advantages.

SUMMARY OF THE INVENTION

The present invention provides materials that include polymers that are reversibly self-associative in response to a stimulus (i.e., stimuli-responsive polymers) and methods for using the materials.

In one aspect, the invention provides a particle including a plurality of polymer-biomolecule conjugates. In the particle, each conjugate includes a polymer covalently coupled to a biomolecule, and the polymer is reversibly self-associative in response to a stimulus. In the particle, the plurality of conjugates are adhered through polymer association. In one embodiment, the particle is a nanoparticle. In another embodiment, the particle is a microparticle. The particle size can range from about 50 to about 1000 nm.

The polymer-biomolecule conjugate comprises a polymer covalently coupled to a biomolecule, wherein the polymer is reversibly self-associative in response to a stimulus. The polymer has a first state in which the polymer is not self-associative, and a second state in which the polymer is self-associative. The polymer adopts the second state in response to a stimulus, and reverts to the first state from the second state on removal of the stimulus. In one embodiment, the polymer is a temperature-sensitive polymer. In another embodiment, the polymer is a pH-sensitive polymer. In another embodiment, the polymer is a light-sensitive polymer. The biomolecule can be a protein or a peptide, such as an enzyme, antibody, or affinity protein; a nucleic acid, such as a DNA or an RNA; a carbohydrate, such as a polysaccharide; or other biochemical species.

In another aspect of the invention, a modified bead is provided. The bead includes a target binding partner and a polymer. The target binding partner is capable of forming an associative interaction with a target compound, and the polymer is reversibly associative in response to a stimulus. In one embodiment, each of the target binding partner and polymer is covalently coupled to the bead. In one embodiment, the bead further includes a second polymer reversibly responsive to a second stimulus and a second target binding partner that forms an associative interaction with a second target compound. In other embodiments, the bead includes a plurality of different target binding partners and a plurality of different polymers.

In another aspect, the present invention provides methods for immobilizing particles on and releasing particles from a substrate. In one embodiment, the method includes the steps of:

(a) contacting a substrate with a plurality of particles, wherein each particle comprises a polymer that is reversibly associative in response to a stimulus; and (b) applying a stimulus effective in associating at least some of the plurality of particles to the substrate to immobilize at least some of the particles to provide immobilized particles, wherein the immobilized particles are immobilized on the substrate through an associative interaction with polymer.

In one embodiment, each particle further comprises a target binding partner. In one embodiment, the method further includes removing the stimulus effective in immobilizing the particle to the substrate, thereby reversing the associative interaction between the polymer and the substrate and releasing the particles from the substrate.

In another aspect of the invention, a method for isolating a target compound is provided. The method includes the steps of:

(a) contacting an immobilized target binding partner with a sample containing a target compound to provide an immobilized target compound, wherein the immobilized target binding partner comprises a particle to which are attached a target binding partner and a polymer that is reversibly associative in response to a stimulus, and wherein the particle is immobilized on a substrate through an associative interaction with polymer; and (b) applying a stimulus effective in reversing the associative interaction between the polymer and the substrate thereby releasing the immobilized target compound from the substrate.

In the method, the target compound and target binding partner are a binding pair, which means that each has an affinity toward the other (e.g., antigen and antibody). In one embodiment, the target compound is an antibody and the target binding partner is an antigen. In another embodiment, the target compound is a protein and the target binding partner is protein. In another embodiment, the target compound is a nucleic acid and the target binding partner is a complimentary nucleic acid. In another embodiment, the target compound is an enzyme and the target binding partner is a substrate.

In another aspect of the invention, a method for concentrating a target compound is provided. The method includes the steps of:

(a) contacting an immobilized target binding partner with a sample containing a target compound and having a first target compound concentration to provide an immobilized target compound, wherein the immobilized target binding partner comprises a particle to which are attached a target binding partner and a polymer, wherein the polymer is reversibly associative in response to a stimulus, and wherein the particle is immobilized on a substrate through an associative interaction with polymer; and (b) applying a stimulus effective in reversing the associative interaction between the polymer and the substrate thereby releasing the immobilized target compound from the substrate to provide a product containing the target compound and having a second target compound concentration, wherein the second target compound concentration is greater than the first target compound concentration.

In another aspect of the invention, a method for performing an assay (i.e., determining and/or quantitating the presence of a target compound) is provided. In one embodiment, the method includes the steps of:

(a) contacting an immobilized target binding partner with a sample containing a target compound to provide an immobilized target compound, wherein the immobilized target binding partner comprises a particle to which are attached a target binding partner and a polymer that is reversibly associative in response to a stimulus, and wherein the particle is immobilized on a substrate through an associative interaction with polymer;

(b) contacting the immobilized target compound with a reporter agent to provide an immobilized target compound with bound reporter agent, wherein the reporter agent provides a signal for detecting the presence of the target compound;

(c) applying a stimulus effective in reversing the associative interaction between the polymer and the substrate thereby releasing the immobilized target compound with bound reporting agent from the substrate to provide a released target compound with bound reporting agent; and (d) analyzing the released target compound with bound reporting agent to detect the presence of the target compound.

In one embodiment, the method includes the steps of:

(a) contacting an immobilized target binding partner with a sample containing a target compound to provide an immobilized target compound, wherein the immobilized target binding partner comprises a particle to which are attached a target binding partner and a polymer, and wherein the particle is immobilized on a substrate through an associative interaction with the polymer;

(b) contacting the immobilized target compound with a reporter agent to provide an immobilized target compound with bound reporter agent, wherein the reporter agent provides a signal for detecting the presence of the target compound; and (d) analyzing the immobilized target compound with bound reporting agent to detect the presence of the target compound.

In another aspect, the invention provide devices that include polymers that are reversibly self-associative in response to a stimulus. In one embodiment, the device includes a surface modified with a polymer covalently coupled to the surface. In one embodiment, the surface is a microfluidic channel surface.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A illustrates a conjugate having the polymer conjugated to the biomolecule proximate to its active site (10B); FIG. 1B illustrates a conjugate having the polymer conjugated to the biomolecule away from its active site (10A);

FIG. 2A illustrates a conjugate having the polymer conjugated to the biomolecule proximate to its active site (11B); FIG. 2B illustrates a conjugate having the polymer conjugated to the biomolecule away from its active site (11A);

FIG. 9A illustrates a bead surface (102) modified with a stimuli-responsive polymer (200); and FIG. 9B illustrates a bead surface (102) modified with a stimuli-responsive polymer (200) and a modified polyethylene glycol polymer (300);

DETAILED DESCRIPTION OF THE PREFERRED EMBODIMENT

Figure 1A:
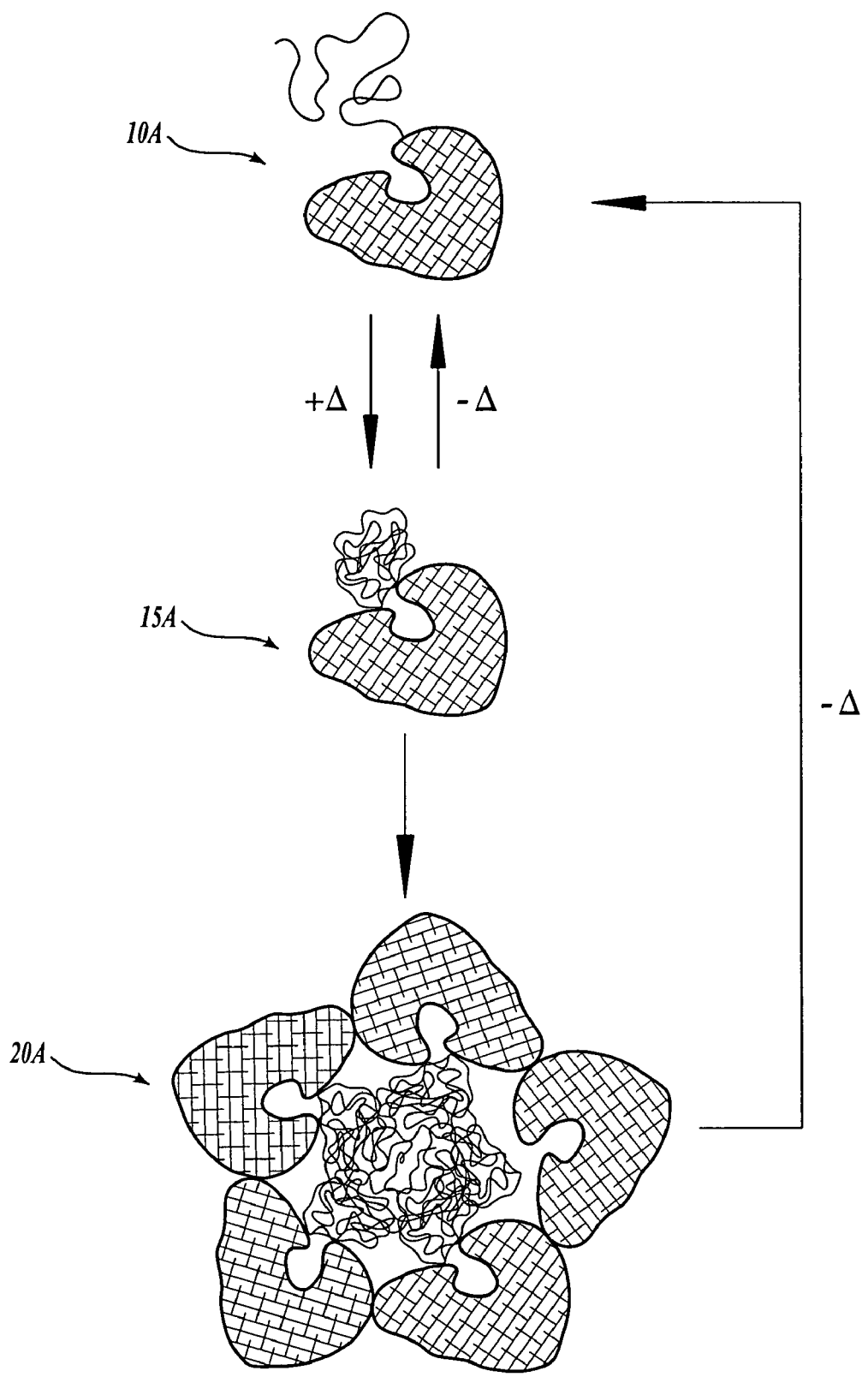
FIGS. 1A and 1B are illustrations of a stimuli-responsive polymer-biomolecule (affinity protein) conjugates forming representative particles (20A and 20B) of the invention that include a plurality of conjugates adhered through polymer association caused by the application of a stimulus; application of a stimulus to a conjugate in its non-associative state (10A and 10B) provides a conjugate in its associative state (15A and 15B); removal of the stimulus dissociates the particle and regenerates the conjugate in its non-associative state.
Figure 1B:
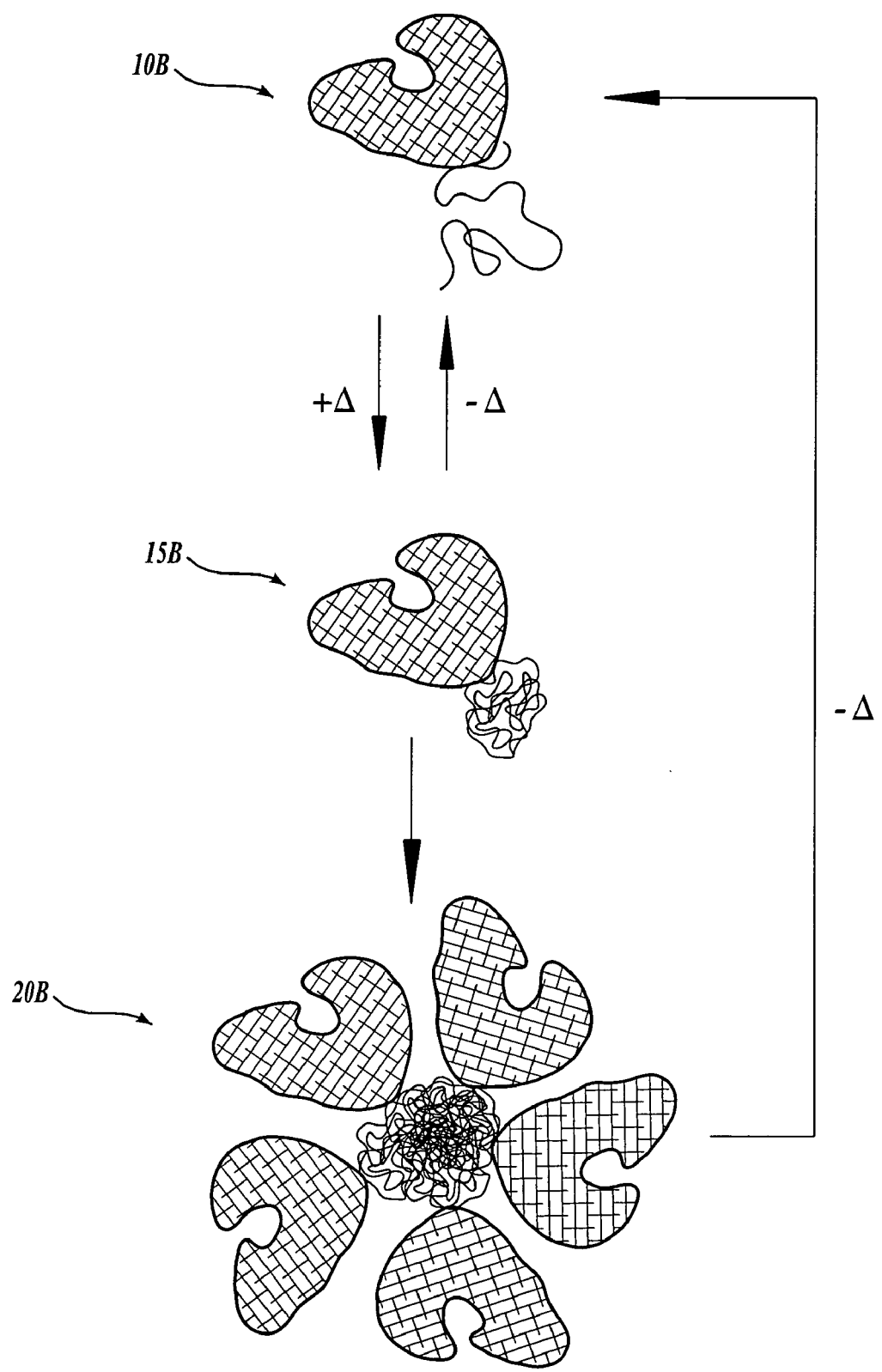
Figure 2A:
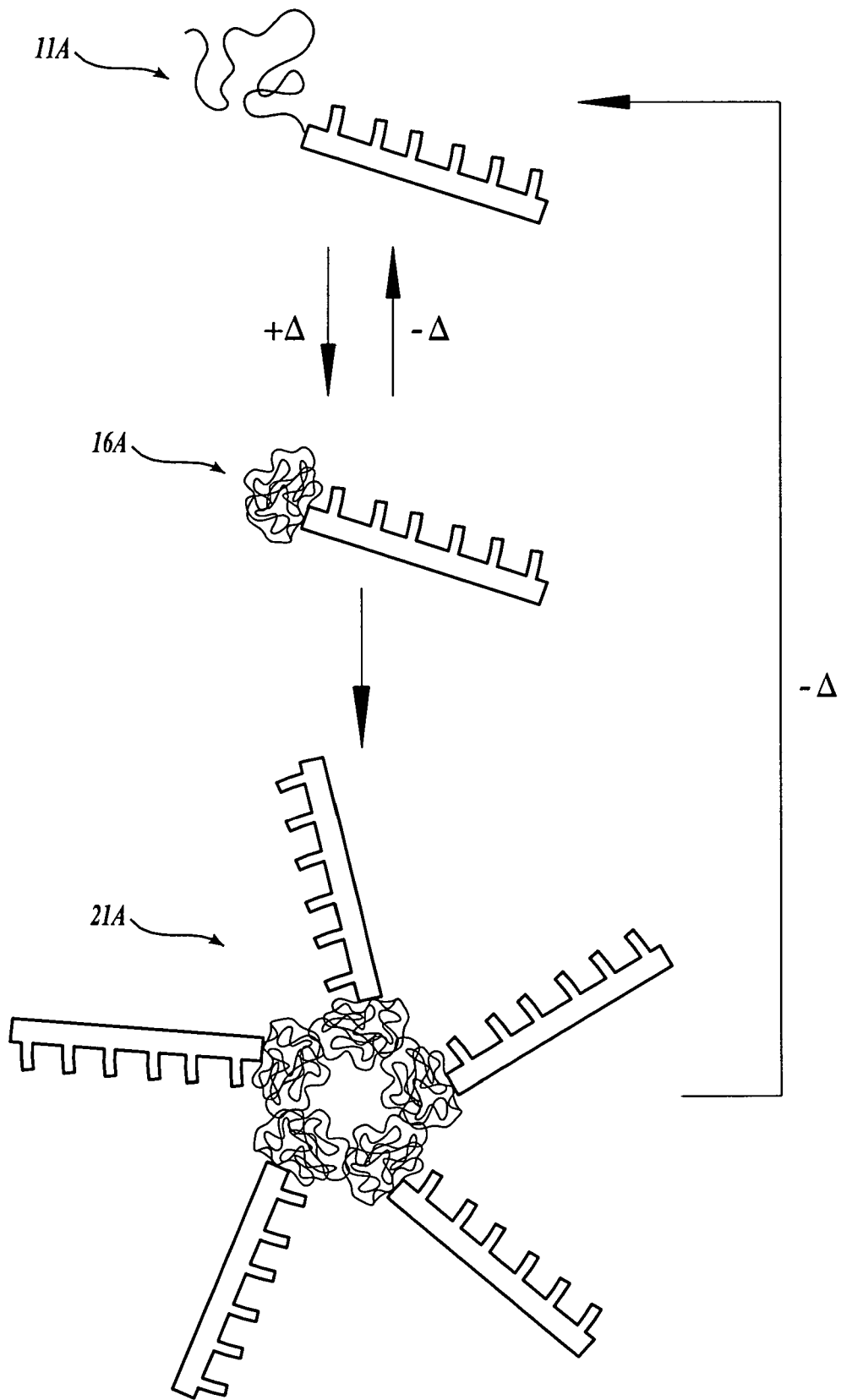
FIGS. 2A and 2B are illustrations of a stimuli-responsive polymer-biomolecule (nucleic acid oligomer) conjugates forming representative particles (21A and 21B) of the invention that includes a plurality of conjugates adhered through polymer association caused by the application of a stimulus; application of a stimulus to a conjugate in its non-associative state (11A and 11B) provides a conjugate in its associative state (16A and 16B); removal of the stimulus dissociates the particle and regenerates the conjugate in its non-associative state.
Figure 2B:
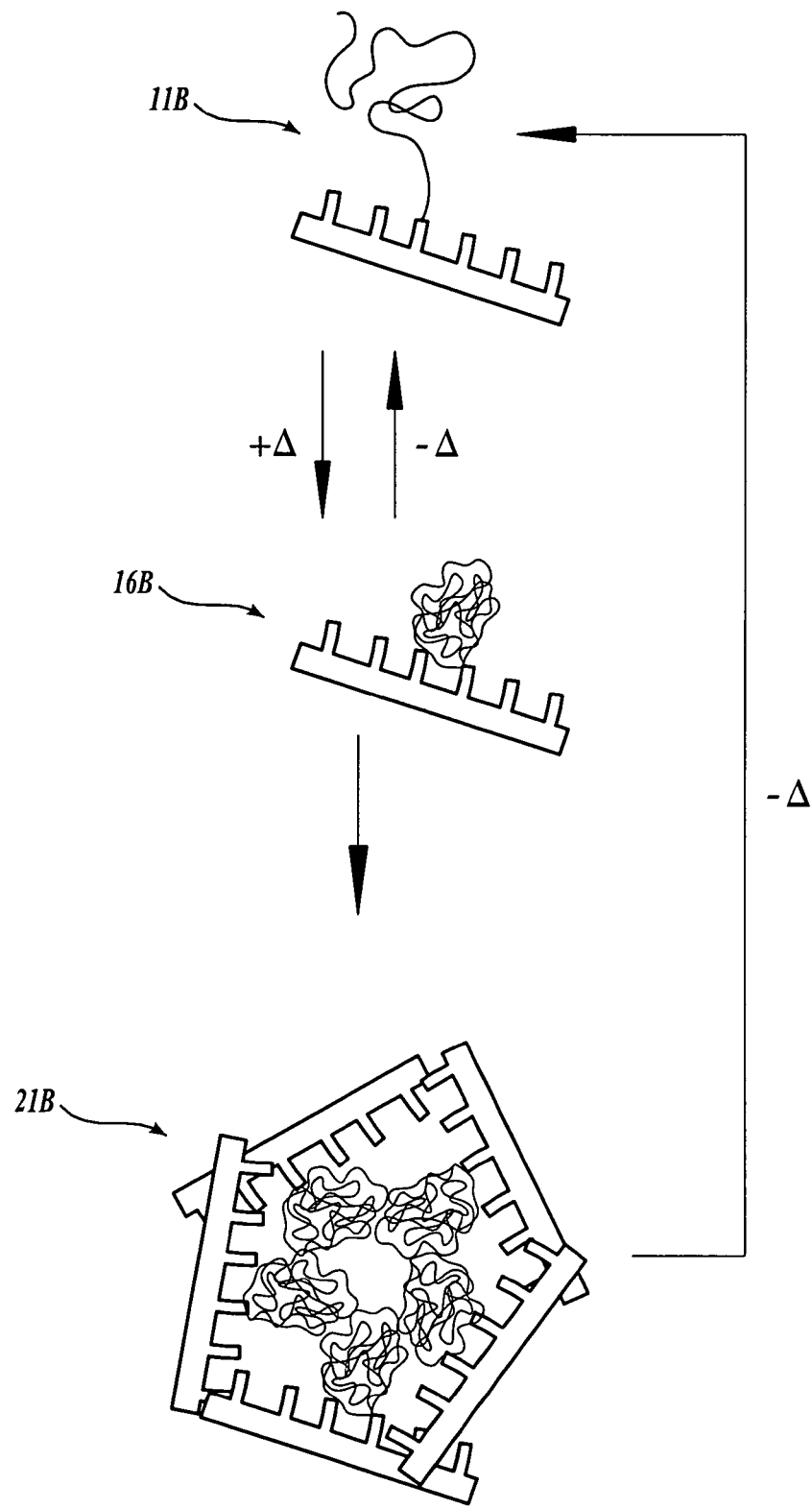

The present invention provides materials that include polymers that are reversibly self-associative in response to a stimulus (i.e., stimuli-responsive polymers) and methods for using the materials.

Stimuli-Responsive Polymer Conjugates

The present invention utilizes a stimuli-responsive polymer conjugate. The conjugate includes a polymer covalently coupled to a biomolecule, wherein the polymer is reversibly self-associative in response to a stimulus. The polymer has a first state in which the polymer is not self-associative, and a second state in which the polymer is self-associative. The polymer adopts the second state in response to a stimulus, and reverts to the first state from the second state on removal of the stimulus. The stimuli-responsive polymer imparts stimuli responsiveness to the conjugate.

The stimuli-response polymer can be any one of a variety of polymers that change their associative properties (e.g., change from hydrophilic to hydrophobic) in response to a stimulus (e.g., temperature, pH, wavelength of light, ion concentration). The stimuli-responsive polymers are synthetic or natural polymers that exhibit reversible conformational or physico-chemical changes such as folding/unfolding transitions, reversible precipitation behavior, or other conformational changes in response to changes in temperature, light, pH, ions, or pressure. Representative stimuli-responsive polymers include temperature-sensitive polymers, a pH-sensitive polymers, and a light-sensitive polymers.

Stimulus-responsive polymers useful in making the conjugates and materials described herein can be any which are sensitive to a stimulus that cause significant conformational changes in the polymer. Illustrative polymers described herein include temperature-, pH-, ion- and/or light-sensitive polymers. Hoffman, A. S., "Intelligent Polymers in Medicine and Biotechnology", *Artif. Organs.* 19:458-467 (1995); Chen, G. H. and A. S. Hoffman, "A New Temperature- and Ph-Responsive Copolymer for Possible Use in Protein Conjugation", *Macromol. Chem. Phys.* 196:1251-1259 (1995); Irie, M. and D. Kungwatchakun, "Photoresponsive Polymers. Mechanochemistry of Polyacrylamide Gels Having Triphenylmethane Leuco Derivatives", *Maokromol. Chem., Rapid Commun* 5:829-832 (1985); and Irie, M., "Light-induced Reversible Conformational Changes of Polymers in Solution and Gel Phase", *ACS Polym. Preprints,* 27(2):342-343 (1986); which are incorporated by reference herein.

Stimuli-responsive oligomers and polymers useful in the conjugates and materials described herein can be synthesized that range in molecular weight from about 1,000 to 30,000 Daltons. In a preferred embodiment, these syntheses are based on the chain transfer-initiated free radical polymerization of vinyl-type monomers, as described herein, and by (1) Tanaka, T., "Gels", *Sci. Amer.* 244:124-138 (1981); 2) Osada, Y. and S. B. Ross-Murphy, "Intelligent Gels", *Sci. Amer,* 268:82-87 (1993); (3) Hoffman, A. S., "Intelligent Polymers in Medicine and Biotechnology", *Artif. Organs* 19:458-467 (i995); also *Macromol. Symp.* 98:645-664 (1995); (4) Feijen, J., I. Feil, F. J. van der Gaag, Y. H. Bae and S. W. Kim, "Thermosensitive Polymers and Hydrogels Based on N-isopropylacrylamide", 11*th European Conf. on Biomtls:* 256-260 (1994); (5) Monji, N. and A. S. Hoffman, "A Novel Immunoassay System and Bioseparation Process Based on Thermal Phase Separating Polymers", *Appl. Biochem. and Biotech.* 14:107-120 (1987); (6) Fujimura, M., T. Mori and T. Tosa, "Preparation and Properties of Soluble-Insoluble Immobilized Proteases", *Biotech. Bioeng.* 29:747-752 (1987); (7) Nguyen, A. L. and J. H. T. Luong, "Synthesis and Applications of Water-Soluble Reactive Polymers for Purification and Immobilization of Biomolecules", *Biotech. Bioeng.* 34:1186-1190 (1989); (8) Taniguchi, M., M. Kobayahi and M. Fujii, "Properties of a Reversible Soluble-Insoluble Cellulase and Its Application to Repeated Hydrolysis of Crystalline Cellulose", *Biotech. Bioeng.* 34:1092-1097 (1989); (9) Monji, N., C-A. Cole, M. Tam, L. Goldstein, R. C. Nowinski and A. S. Hoffman, "Application of a Thermally-Reversible Polymer-Antibody Conjugate in a Novel Membrane-Based Immunoassay", *Biochem. and Biophys. Res. Comm.* 172:652-660 (1990); (10) Monji, N. C. A. Cole, and A. S. Hoffman, "Activated, N-Substituted Acrylamide Polymers for Antibody Coupling: Application to a Novel Membrane-Based Immunoassay", *J. Biomtls. Sci. Polymer Ed.* 5:407-420 (1994); (11) Chen, J. P. and A. S. Hoffman, "Polymer-Protein Conjugates: Affinity Precipitation of Human IgG by Poly(N-Isopropyl Acrylamide)-Protein A Conjugates", *Biomtls.* 11:631-634 (1990); (12) Park, T. G. and A. S. Hoffman, "Synthesis and Characterization of a Soluble, Temperature-Sensitive Polymer-Conjugated Enzyme, *J. Biomtls. Sci. Polymer Ed.* 4:493-504 (1993); (13) Chen, G. H., and A. S. Hoffman, Preparation and Properties of Thermo-Reversible, Phase-Separating Enzyme-Oligo(NIPAAm) Conjugates", *Bioconj. Chem.* 4:509-514 (1993); (14) Ding, Z. L., G. H. Chen, and A. S. Hoffman, "Synthesis and Purification of Thermally-Sensitive Oligomer-Enzyme Conjugates of Poly (NIPAAm)-Trypsin", *Bioconj. Chem.* 7: 121-125 (1995); (15) Chen, G. H. and A. S. Hoffman, "A New Temperature- and pH-Responsive Copolymer for Possible Use in Protein Conjugation", *Macromol. Chem. Phys.* 196:1251-1259 (1995); (16) Takei, Y. G., T. Aoki, K. Sanui, N. Ogata, T. Okano, and Y. Sakurai, "Temperature-responsive Bioconjugates. 1. Synthesis of Temperature-Responsive Oligomers with Reactive End Groups and their Coupling to Biomolecules", Bioconj. Chem., 4, 42-46 (1993); (17) Takei, Y. G., T. Aoki, K. Sanui, N. Ogata, T. Okano and Y. Sakurai, "Temperature-responsive Bioconjugates. 2. Molecular Design for Temperature-modulated Bioseparations", Bioconj. Chem., 4, 341-346 (1993); (18) Takei, Y. G., M. Matsukata, T. Aoki, K. Sanui, N. Ogata, A. Kikuchi, Y. Sakurai and T. Okano, "Temperature-responsive Bioconjugates. 3. Antibody-Poly(N-isopropylacrylamide) Conjugates for Temperature-Modulated Precipitations and Affinity Bioseparations", Bioconj. Chem., 5, 577-582 (1994); (19) Matsukata, M., Y. Takei, T. Aoki, K. Sanui, N. Ogata, Y. Sakurai and T. Okano, "Temperature Modulated Solubility-Activity Alterations for Poly(N-Isopropylacrylamide)-Lipase Conjugates", J. Biochem., 116, 682-686 (1994); (20) Chilkoti, A., G. H. Chen, P. S. Stayton and A. S. Hoffman, "Site-Specific Conjugation of a Temperature-Sensitive Polymer to a Genetically-Engineered Protein", *Bioconj. Chem.* 5:504-507 (1994); and (21) Stayton, P. S., T. Shimoboji, C. Long, A. Chilkoti, G. Chen, J. M. Harris and A. S. Hoffman, "Control of Protein-Ligand Recognition Using a Stimuli-Responsive Polymer", *Nature* 378:472-474 (1995).

These types of monomers allow the design of copolymer compositions to respond to a specific stimulus and, in some embodiments, to two or more stimuli. In addition, control of molecular weight (by control of reactant concentrations and reaction conditions), composition, structure (e.g., linear homopolymer, linear copolymer, block or graft copolymer, "comb" polymers and "star" polymers) and type and number of reactant end groups permit "tailoring" of the appropriate polymer for conjugation to a specific site on the biomolecule or particle.

The stimuli-responsive polymers useful in the materials and methods of the invention include homopolymers and copolymers having stimuli responsive behavior. Other suitable stimuli-responsive polymers include block and graft copolymers having one or more stimuli-responsive polymer components. A suitable stimuli-responsive block copolymer may include, for example, a temperature-sensitive polymer block. A suitable stimuli-responsive graft copolymer may include, for example, a pH-sensitive polymer backbone or pendant temperature-sensitive polymer components.

Temperature-Sensitive Polymers. Illustrative embodiments of the many different types of temperature-sensitive polymers that may be conjugated to interactive molecules are polymers and copolymers of N-isopropyl acrylamide (NIPAAm). PolyNIPAAm is a thermally sensitive polymer that precipitates out of water at 32° C., which is its lower critical solution temperature (LCST), or cloud point (Heskins and Guillet, J. Macromol. *Sci.-Chem. A*2:1441-1455 (1968)). When polyNIPAAm is copolymerized with more hydrophilic comonomers such as acrylamide, the LCST is raised. The opposite occurs when it is copolymerized with more hydrophobic comonomers, such as N-t-butyl acrylamide. Copolymers of NIPAAm with more hydrophilic monomers, such as AAm, have a higher LCST, and a broader temperature range of precipitation, while copolymers with more hydrophobic monomers, such as N-t-butyl acrylamide, have a lower LCST and usually are more likely to retain the sharp transition characteristic of PNIPAAm (Taylor and Cerankowski, *J. Polymer Sci.* 13:2551-2570 (1975); Priest et al., *ACS Symposium Series* 350:255-264 (1987); and Heskins and Guillet, J. Macromol. *Sci.-Chem. A*2:1441-1455 (1968), the disclosures of which are incorporated herein). Copolymers can be produced having higher or lower LCSTs and a broader temperature range of precipitation.

Stimuli-responsive polymers such as poly(NIPAAm) have been conjugated randomly to affinity molecules, such as monoclonal antibodies, for example, as described in U.S. Pat. No. 4,780,409; Monji and Hoffman, *Appl. Biochem. Biotechnol.* 14:107-120 (1987). Activated groups (e.g, for conjugating to proteins), were formed randomly along the backbone of PNIPAAm and were conjugated randomly to lysine amino groups on a monoclonal antibody and the conjugate was then applied in a temperature-induced phase-separation immunoassay. Activated PNIPAAm has also been conjugated by Hoffman and coworkers to protein A, various enzymes, biotin, phospholipids, RGD peptide sequences, and other interactive molecules. The random polymer-interactive molecular conjugates have been used in a variety of applications based on the thermally-induced phase separation step (Chen and Hoffman, *Biomaterials* 11:631-634 (1990); Miura et al., *Abstr. 17th Ann. Meet. Soc. Biomaterials* (1991); Wu et al., *Polymer* 33:4659-4662 (1992); Chen and Hoffman, *Bioconjugate Chem.* 4:509-514 (1993); Morris et al., *J. Anal. Biochem.* 41:991-997 (1993); Park and Hoffman, *J. Biomaterials Sci. Polymer Ed.* 4:493-504 (1993); Chen and Hoffman, *J. Biomaterials Sci. Polymer Ed.* 5:371-382 (1994)). Others have also randomly conjugated proteins to PNIPAAm (Nguyen and Luong, *Biotech. Bioeng.* 34:1186-1190 (1989); Takei et al., *Bioconj. Chem.* 4:42-46 (1993)) and to pH-sensitive polymers (Fujimura et al., supra.)). Most of these polymer-protein conjugates involved random lysine amino groups of proteins bound to the polymer through random activated groups pendant along the polymer backbone. More recently, a new method based on chain transfer initiation polymerization has been used which yields relatively low MW polymers (called oligomers) usually with only one reactive end group (but the method may be adapted to synthesis of oligomers with a reactive group at each end) (Otsu, T., et al., *Eur. Polym. J.* 28:1325-1329, (1992)). (Chen and Hoffman, 1993, supra; Chen and Hoffman, 1994, supra, and Takei et al., supra). The synthesis of an amino-terminated polymer proceeds by the radical polymerization of NIPAAm in the presence of AIBN as an initiator and 1-aminoethanethiol-hydrochloride as a chain transfer reagent. To synthesize a chain with —COOH or —OH terminal groups, carboxyl- or hydroxyl-thiol chain transfer agents, respectively, have been used instead of the amino-thiol. It should be noted that the synthesis of the end-reactive polymers is based on a chain transfer initiation and termination mechanism. This yields a relatively short polymer chain, having a molecular weight somewhere between 1000 and 25,000 to 30,000. The shortest chains, less than 10,000 in molecular weight, are usually called "oligomers". Oligomers of different molecular weights can be synthesized by simply changing the ratio of monomer to chain transfer reagent, and controlling their concentration levels, along with that of the initiator.

Oligomers of NIPAAm (or other vinyl monomers) having a reactive group at one end are prepared by the radical polymerization of NIPAAm using AIBN as initiator, plus a chain transfer agent with a thiol (—SH) group at one end and the desired "reactive" group (e.g., —OH, —COOH, —NH$_2$) at the other end. Chen and Hoffman, *Bioconjugate Chem.* 4:509-514 (1993) and Chen and Hoffman, *J. Biomaterials Sci. Polymer Ed.* 5:371-382 (1994), each of which is incorporated herein by reference. Appropriate quantities of NIPAAm, AIBN and chain transfer reagent in DMF are placed in a thick-walled polymerization tube and the mixtures are degassed by freezing and evacuating and then thawing (4 times). After cooling for the last time, the tubes are evacuated and sealed prior to polymerization. The tubes are immersed in a water bath at 60° C. for 4 h. The resulting polymer is isolated by precipitation into diethyl ether and weighed to determine yield. The molecular weight of the polymer is determined either by titration (if the end group is amine or carboxyl) or by vapor phase osmometry (VPO).

The molecular weight of vinyl-type copolymers can be controlled by varying the concentration of the key reactants and the polymerization conditions. However, it is difficult to achieve molecular weights much above about 30 kD using synthesis of vinyl-based oligomers by chain transfer initiation. Further, since the amino-thiol chain transfer agent yields a broader molecular weight distribution than the hydroxyl or carboxylthiols (which may be undesirable), the —COOH-terminated polymer can be synthesized and the —COOH end group converted to an amine group by activating with carbodiimide and coupling a diamine to the active ester group.

Temperature sensitive oligopeptides also may be incorporated into the conjugates.

pH-Sensitive Polymers. Synthetic pH-sensitive polymers useful in making the conjugates described herein are typically based on pH-sensitive vinyl monomers, such as acrylic acid (AAc), methacrylic acid (MAAc) and other alkyl-substituted acrylic acids, maleic anhydride (MAnh), maleic acid (MAc), AMPS (2-Acrylamido-2-Methyl-1-Propanesulfonic Acid), N-vinyl formamide (NVA), N-vinyl acetamide (NVA) (the last two may be hydrolysed to polyvinylamine after polymerization), aminoethyl methacrylate (AEMA), phosphoryl ethyl acrylate (PEA) or methacrylate (PEMA). pH-Sensitive polymers may also be synthesized as polypeptides from amino acids (e.g., polylysine or polyglutamic acid) or derived from naturally-occurring polymers such as proteins (e.g., lysozyme, albumin, casein), or polysaccharides (e.g., alginic acid, hyaluronic acid, carrageenan, chitosan, carboxymethyl cellulose) or nucleic acids, such as DNA. pH-Responsive polymers usually contain pendant pH-sensitive groups such as —OPO(OH)$_2$, —COOH or —NH$_2$ groups. With pH-responsive polymers, small changes in pH can stimulate phase-separation, similar to the effect of temperature on solutions of PNIPAAm (Fujimura et al. *Biotech. Bioeng.* 29:747-752 (1987)). By randomly copolymerizing a thermally-sensitive NIPAAm with a small amount (e.g., less than 10 mole percent) of a pH-sensitive comonomer such as AAc, a copolymer will display both temperature and pH sensitivity. Its LCST will be almost unaffected, sometimes even lowered a few degrees, at pHs where the comonomer is not ionized, but it will be dramatically raised if the pH-sensitive groups are ionized. When the pH-sensitive monomer is present in a higher content, the LCST response of the temperature sensitive component may be "eliminated" (e.g., no phase separation seen up to and above 100° C.).

Graft and block copolymers of pH and temperature sensitive monomers can be synthesized which retain both pH and temperature transitions independently. Chen, G. H., and A. S. Hoffman, *Nature* 373:49-52 (1995). For example, a block copolymer having a pH-sensitive block (polyacrylic acid) and a temperature sensitive block (PNIPAAm) can be useful in the conjugates, materials, and methods of the invention.

Light-Sensitive Polymers. Light-responsive polymers usually contain chromophoric groups pendant to or along the main chain of the polymer and, when exposed to an appropriate wavelength of light, can be isomerized from the trans to the cis form, which is dipolar and more hydrophilic and can cause reversible polymer conformational changes. Other light sensitive compounds can also be converted by light stimulation from a relatively non-polar hydrophobic, non-ionized state to a hydrophilic, ionic state.

In the case of pendant light-sensitive group polymers, the light-sensitive dye, such as aromatic azo compounds or stilbene derivatives, may be conjugated to a reactive monomer (an exception is a dye such as chlorophyllin, which already has a vinyl group) and then homopolymerized or copolymerized with other conventional monomers, or copolymerized with temperature-sensitive or pH-sensitive monomers using the chain transfer polymerization as described above. The light sensitive group may also be conjugated to one end of a different (e.g., temperature) responsive polymer. A number of protocols for such dye-conjugated monomer syntheses are known. Kungwatchakun and Irie, supra, and Mamada et al., supra.

Although both pendant and main chain light sensitive polymers may be synthesized and are useful compositions for the methods and applications described herein, the preferred light-sensitive polymers and copolymers thereof are typically synthesized from vinyl monomers that contain light-sensitive pendant groups. Copolymers of these types of monomers are prepared with "normal" water-soluble comonomers such as acrylamide, and also with temperature- or pH-sensitive comonomers such as NIPAAm or AAc.

Light-sensitive compounds may be dye molecules that isomerize or become ionized when they absorb certain wavelengths of light, converting them from hydrophobic to hydrophilic conformations, or they may be other dye molecules which give off heat when they absorb certain wavelengths of light. In the former case, the isomerization alone can cause chain expansion or collapse, while in the latter case the polymer will precipitate only if it is also temperature-sensitive.

Light-responsive polymers usually contain chromophoric groups pendant to the main chain of the polymer. Typical chromophoric groups that have been used are the aromatic diazo dyes (Ciardelli, *Biopolymers* 23:1423-1437 (1984); Kungwatchakun and Irie, *Makromol. Chem., Rapid Commun.* 9:243-246 (1988); Lohmann and Petrak, *CRC Crit. Rev. Therap. Drug Carrier Systems* 5:263 (1989); Mamada et al., *Macromolecules* 23:1517 (1990), each of which is incorporated herein by reference). When this type of dye is exposed to 350-410 nm UV light, the trans form of the aromatic diazo dye, which is more hydrophobic, is isomerized to the cis form, which is dipolar and more hydrophilic, and this can cause polymer conformational changes, causing a turbid polymer solution to clear, depending on the degree of dye-conjugation to the backbone and the water solubility of the main unit of the backbone. Exposure to about 750 nm visible light will reverse the phenomenon. Such light-sensitive dyes may also be incorporated along the main chain of the backbone, such that the conformational changes due to light-induced isomerization of the dye will cause polymer chain conformational changes. Conversion of the pendant dye to a hydrophilic or hydrophobic state can also cause individual chains to expand or collapse their conformations. When the polymer main chain contains light sensitive groups (e.g. azo benzene dye) the light-stimulated state may actually contract and become more hydrophilic upon light-induced isomerization. The light-sensitive polymers can include polymers having pendant or backbone azobenzene groups.

Specific Ion-Sensitive Polymers. Polysaccharides, such as carrageenan, that change their conformation, for example, from a random to an ordered conformation, as a function of exposure to specific ions, such as $K^+$ or $Ca^{++}$, can also be used as the stimulus-responsive polymers. In another example, a solution of sodium alginate may be gelled by exposure to $Ca^{++}$. Other specific ion-sensitive polymers include polymers with pendant ion chelating groups, such as histidine or EDTA.

Dual- or Multi-Sensitivity Polymers. If a light-sensitive polymer is also thermally-sensitive, the UV- or visible light-stimulated conversion of a chromophore conjugated along the backbone to a more hydrophobic or hydrophilic conformation can also stimulate the dissolution or precipitation of the copolymer, depending on the polymer composition and the temperature. If the dye absorbs the light and converts it to thermal energies rather than stimulating isomerization, then the localized heating can also stimulate a phase change in a temperature-sensitive polymer such as PNIPAAm, when the system temperature is near the phase separation temperature. The ability to incorporate multiple sensitivities, such as temperature and light sensitivity, or temperature and pH sensitivity, along one backbone by vinyl monomer copolymerization lends great versatility to the synthesis and properties of the responsive polymer-protein conjugates. For example, dyes can be used which bind to protein recognition sites, and light-induced isomerization can cause loosening or detachment of the dye from the binding pocket (Bieth et al., *Proc. Natl. Acad. Sci. USA* 64:1103-1106 (1969)). This can be used for manipulating affinity processes by conjugating the dye to the free end of a temperature responsive polymer, such as ethylene oxide-propylene oxide (EO-PO) random copolymers available from Carbide. These polymers, $-(CH_2CH_2O)_x-(CH_2CHCH_3O)_y-$, have two reactive end groups. The phase separation point can be varied over a wide range, depending on the EO/PO ratio, and one end may be derivatized with the ligand dye and the other end with an —SH reactive group, such as vinyl sulfone (VS).

The conjugates of the invention can include a biomolecule (e.g., target binding partner). The biomolecule can be a protein or a peptide, such as an enzyme, antibody, or affinity protein; a nucleic acid oligomer, such as a DNA or an RNA; a carbohydrate, such as a polysaccharide; or other biochemical species. The biomolecule can have an active site, and the polymer can be covalently coupled to the biomolecule at a site proximate to the active site such that, when the polymer is self-associative, the binding site is inaccessible. Alternatively, the polymer is covalently coupled to the biomolecule at a site away from the active site such that, when the polymer is self-associative, the binding site is accessible.

The term "biomolecule molecule" as used herein includes any molecule capable of a specific binding interaction with a target site, for example on a cell membrane, or on a molecule or atom. Thus, biomolecules include both ligands and receptors.

The stimulus-responsive polymer can be conjugated to a variety of different biomolecules, including peptides, proteins, poly- or oligo-saccharides, glycoproteins, lipids and lipoproteins, and nucleic acids, as well as synthetic organic or inorganic molecules having a defined bioactivity, such as an antibiotic or antiinflammatory agent, and which bind to a target site, for example, on a molecule such as a cell membrane receptor. Examples of protein biomolecules are ligand-binding proteins, including antibodies, lectins, hormones, and receptors, and enzymes. Other molecules which bind specifically or non-specifically to a target compound include poly- or oligosaccharides on glycoproteins which bind to receptors, for example, the carbohydrate on the ligand for the inflammatory mediators P-selectin and E-selectin, and nucleic acid sequences which bind to complementary sequences, such as ribozymes, antisense, external guide sequences for RNAase P, and aptamers.

The biomolecules can include a binding site, which may be the active site of an antibody or enzyme, the binding region of a receptor, or other functionally equivalent site. These sites are collectively referred to as the binding site.

The number of proteins whose interaction with specific binding partners can be controlled via site-specific conjugation of a stimulus-responsive polymer is quite large. These include, for example, antibodies (monoclonal, polyclonal, chimeric, single-chain or other recombinant forms), their protein/peptide antigens, protein/peptide hormones, streptavidin, avidin, protein A, protein G, growth factors and their respective receptors, DNA-binding proteins, cell membrane receptors, endosomal membrane receptors, nuclear membrane receptors, neuron receptors, visual receptors, and muscle cell receptors. Oligonucleotides which can be modified include DNA (genomic or cDNA), RNA, antisense, ribozymes, and external guide sequences for RNAase P, and can range in size from short oligonucleotide primers up to entire genes. Carbohydrates include tumor associated carbohydrates (e.g., $Le^x$, sialyl $Le^x$, $Le^y$, and others identified as tumor associated as described in U.S. Pat. No. 4,971,905, incorporated herein by reference), carbohydrates associated with cell adhesion receptors (e.g., Phillips et al., *Science* 250:1130-1132 (1990)), and other specific carbohydrate binding molecules and mimetics thereof which are specific for cell membrane receptors.

Among the proteins, streptavidin is particularly useful as a model for other ligand-binding and substrate-binding systems described herein. Streptavidin is an important component in many separations and diagnostic technologies which use the very strong association of the streptavidin-biotin affinity complex. (Wilchek and Bayer, *Avidin-Biotin Technology*, New York, Academic Press, Inc. (1990); and Green, *Meth. Enzymol.* 184:51-67. Protein G, a protein that binds IgG antibodies (Achari et al., *Biochemistry* 31:10449-10457 (1992), and Akerstrom and Bjorck, *J. Biol. Chem.* 261:10240-10247 (1986)) is also useful as a model system. Representative immunoaffinity molecules include engineered single chain Fv antibody (Bird et al., *Science* 242:423-426 (1988) and U.S. Pat. No. 4,946,778 to Ladner et al., incorporated herein by reference, Fab, Fab', and monoclonal or polyclonal antibodies. Enzymes represent another important model system, as their activity can be turned on or off or modulated by the controlled collapse of the stimulus-responsive component at the active site.

In addition to their well established uses in biotechnology, streptavidin, protein G, single-chain antibodies and enzymes are ideal model systems for several other important reasons. Genetic engineering systems for these proteins have been established, allowing convenient site-directed mutagenesis and the expression of large quantities of each protein in hosts such as *E. coli*. High-resolution crystal structures are available that provide a molecular "road map" of the ligand binding sites (Achari et al. supra; Hendrickson et al., *Proc. Natl. Acad. Sci. USA* 86:2190-2194 (1989); Weber et al., *Science* 243:85-88 (1992); Derrick and Wigley, *Nature* 359:752-754 (1992); Mian, *J. Mol. Biol.* 217:133-151 (1991)). This structural information provides a rational basis for the design of affinity or activity switch site-directed mutants. Of course, proteins which already have one, two or more cysteine residues located at a site convenient for attaching a stimulus-responsive component are ready for attachment of the stimulus-responsive component and need not have other cysteine residues engineered therein (unless another thiol group is desired in a specific site or useless reaction of the wild type —SH group undesirably changes the protein bioactivity). Other sites on the proteins can also be used, including amino acids substituted with non-natural amino acids.

Other affinity systems include conconavalin A, which has an affinity to sugars (e.g., mannose, glucose, and galactose).

Stimuli-Responsive Polymer Conjugate Aggregates

In one aspect of the invention, formations (or aggregates) made up of a plurality of polymer-biomolecule conjugates are provided. In the aggregate, each conjugate includes a polymer covalently coupled to a biomolecule, and the polymer is reversibly self-associative in response to a stimulus. In the aggregate, the plurality of conjugates are adhered through polymer association. The aggregate can be controllably formed to have a particle size from about 50 to about 1000 nm. In one embodiment, the aggregate is a nanoparticle. In another embodiment, the aggregate is a microparticle. Because the aggregate is controllably formed by the application of a stimulus to a stimuli-responsive polymer conjugate and through polymer association, the aggregate can be dissociated to its component conjugates by removal of the stimulus causing association. Representative stimuli-responsive polymer aggregates are schematically illustrated in FIGS. 1A (20A), 1B (20B), 2A (21A), 2B (21B), 3 (20A and 20b), and 4 (21A and 21B).

Stimuli-Responsive Polymer Modified Substrate

In another aspect, the invention provides a substrate modified to include a polymer that is reversibly self-associative in response to a stimulus. In one embodiment, the polymer is covalently coupled to the substrate. In another embodiment, the polymer is non-covalently attached to the substrate. The substrate can be a bead or a surface of a channel. Representative stimuli-responsive polymer modified substrates are schematically illustrated in FIGS. 3-6 (see 12 and 13).

Stimuli-Responsive Polymer Modified Beads

In another aspect, the invention provides a bead that has been modified to include a stimuli-responsive polymer. In one embodiment, the bead further includes a target binding partner. The polymer is reversibly associative in response to a stimulus. The target binding partner is capable of forming an associative interaction with a target compound. The stimuli-responsive polymer imparts stimuli responsiveness to the bead. In one embodiment, each of the target binding partner and polymer is covalently coupled to the bead.

Suitable beads include nanometer and microscale beads; gold, semiconductor, and quantum dot beads. The beads can be polymeric beads, such as latex and polystyrene beads.

In one embodiment, the bead further includes a second polymer reversibly responsive to a second stimulus and a second target binding partner that forms an associative interaction with a second target compound. In other embodiments, the bead includes a plurality of different target binding partners and a plurality of different polymers such that multiple target compounds may be isolated from a single (or multiple samples) and then controllably released by the application of specific stimulus.

Methods Employing Stimuli-Responsive Polymer Conjugates and Materials

In other aspects, the invention provides methods that employ stimuli-responsive polymer conjugates and materials.

Immobilization Methods. In one embodiment, the present invention provides a method for immobilizing particles on and releasing particles from a substrate. The method includes the steps of:

(a) contacting a substrate with a plurality of particles, wherein each particle comprises a polymer that is reversibly associative in response to a stimulus; and (b) applying a stimulus effective in associating at least some of the plurality of particles to the substrate to immobilize at least some of the particles to provide immobilized particles, wherein the immobilized particles are immobilized on the substrate through an associative interaction with polymer.

In the method, the substrate may be modified to include a polymer that is reversibly associative in response to a stimulus. Alternatively, the substrate can inherently have the characteristic (e.g., hydrophobicity) of association with the polymer in its associative state.

Figure 5:
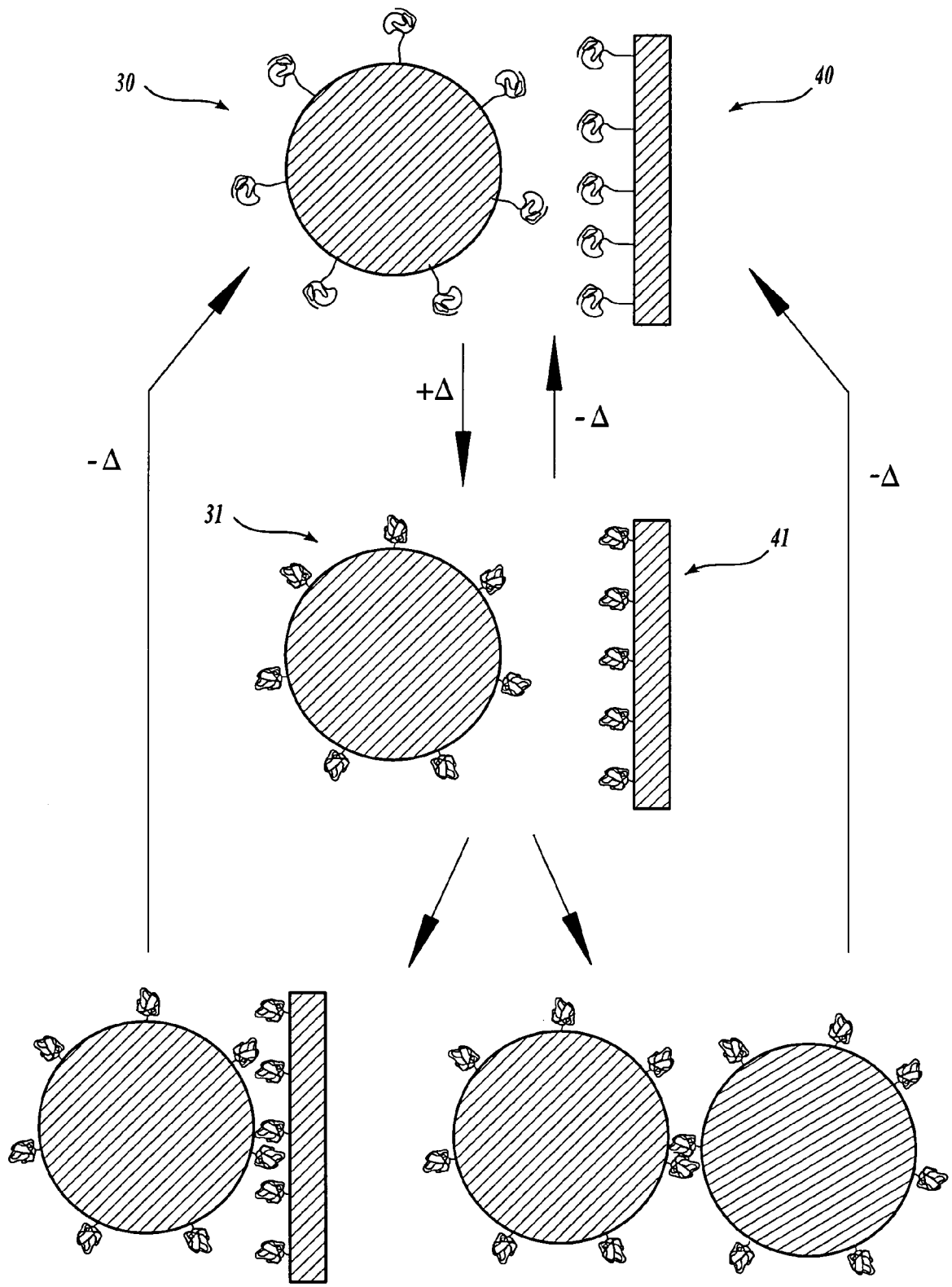
FIG. 5 is an illustration of the association and disassociation of a bead modified to include a polymer that is reversibly associative in response to a stimulus with a substrate modified to include a polymer that is reversibly associative in response to a stimulus; in the absence of stimulus, the bead (30) and substrate (40) are non-associative (e.g., hydrophilic) and non-adherent; in the presence of stimulus, the bead (31) and substrate (41) become associative (e.g., hydrophobic) and adherent to resulting in the association of the bead and substrate, and bead and bead.

FIG. 5 illustrates the interaction of a stimuli-responsive polymer modified particle (e.g., bead) with a stimuli-responsive polymer modified substrate. Application of a stimulus (+Δ) causes bead 30 and substrate 40 to change from their non-associative (i.e., hydrophobic) states to their associative states, 31 and 41, respectively, which can result in the formation of bead-substrate and bead-bead associations.

In one embodiment, each particle further comprises a target binding partner (not illustrated in FIG. 5). Such particles are useful in the methods described below.

To release the immobilized particles, a stimulus effective in reversing the associative interaction between the polymer and the substrate is applied (e.g., removal of the initial stimulus causing association, −Δ), thereby releasing the particles from the substrate.

Methods for Isolation, Concentration, and Determining a Target Compound. In other aspects, the present invention provides methods for (1) isolating a target compound from a sample; (2) concentrating a target compound in a sample; and (3) determining and/or quantitating the presence of a target compound in a sample. The methods are described in detail below. In each of these methods, conjugate or particle immobilization on a substrate occurs through an associative interaction with a stimuli-responsive polymer. As noted above, the substrate may be modified to include a polymer that is reversibly associative in response to a stimulus. See, for example, FIGS. 3-6. Alternatively, the substrate has the inherent characteristic (e.g., hydrophobicity) of association with the polymer in its associative state.

In one aspect, the present invention provides a reversible particle system applicable to a range of particle sizes including, but not limited to nanoparticles, based on conjugates of stimuli-responsive polymers, such as poly(N-isopropylacrylamide) (PNIPAAm), to biomolecules such as proteins and DNA, and/or to particles and beads. Smart polymer-biomolecule and polymer-bead conjugates can be reversibly phase-separated as controlled sized particles that adhere to specially modified device surfaces, or that simply have different diffusive properties based on their aggregated size in microfluidic streams and channels. Beads coated with smart polymers are similarly reversibly aggregated upon the application of the stimulus and the aggregates can be reversibly adhered to device surfaces. Advantages of the conjugates are summarized below.

The stimuli-responsive polymer-biomolecule or polymer-bead conjugates reversibly form nanoparticles and can be aggregated and disaggregated quickly with convenient and biomolecule-friendly signals. Typical stimuli include small changes in temperature, pH or irradiation with different wavelengths of light. The nanoparticles have different diffusive, sedimentation, and adhesive properties compared to the free soluble conjugates that allow their capture and release through application of reversible stimuli. The polymer-biomolecule and bead conjugates may coexist in the same solution, or they may be dissolved or suspended in separate solutions. The solutions may be designed to function in microfluidic channels, chromatography columns, filtration columns, and other devices.

The solutions or suspensions of these species are designed to be used in the channels, columns, and filters where the walls of the devices may in some cases be coated with the same or a different smart polymer. In such a case, a stimulus may convert the surface of the wall from hydrophilic (non-adherent) to hydrophobic (adherent), and then back to hydrophilic when the stimulus is reversed. This could make the particles or the beads adherent or non-adherent to the walls, depending on the conditions. The overall design criterion is that when the polymer is phase separated, it will become hydrophobic, and so the surface of the device wall will be adherent to the particles and beads when their smart polymers are phase separated. The adhesive character of the channel walls will reverse when the stimulus is reversed. The walls of the device may also just simply be constructed of a polymer that is always hydrophobic, such as polyethylene terephthalate (PET) or TEFLON (PTFE). This wall will be adherent to the particles or beads when their polymer coatings are stimulated to become hydrophobic, and the particles or beads will become non-adherent when the stimulus is reversed.

The conjugation site of the smart polymer with the biomolecule may be located at random reactive groups on the surface of biomolecule. It may also be specifically located at surface sites where specific reactive groups have been introduced. For example, the polymer may be specifically conjugated adjacent to the protein's active site, or far away from the active site, by creating mutant proteins with specific reactivities, such as cysteine —SH groups, at those sites.

The stimulus-triggered collapse of the polymer directs the formation of the biomolecule into nanoparticles of controlled size that may be reversibly disaggregated upon reversal of the signal. When the polymer is conjugated site-specifically near the biomolecule's active or recognition site, the orientation of the biomolecule is controlled such that activity or recognition is turned off in the nanoaggregate, and turned on when disaggregated in solution. When the polymer is conjugated site-specifically at a site far from the biomolecule's active or recognition site, then when the polymer is stimulated to collapse, the conjugate will form a nanoparticle and the protein will retain its activity. This is because the biomolecule's active or recognition site is still exposed and is far away from the precipitated polymer, which is at the inner core of the aggregate. This highly active particle may be sequestered to the wall of the channel, or it may remain in solution.

If the conjugate is on the surface of a bead that is modified with the smart polymer, then the reversible formation of the beads may also remove the protein or DNA from solution. The protein or DNA may be either in an active state or inactive state in the aggregated beads. Each of these situations can provide separate and distinct advantages for various end use applications. The phase separation of the beads and conjugates may also lead to reversible binding of the beads and conjugates to device walls or membranes. The aggregates of the conjugates and beads would also be expected to diffuse and sediment differently from the soluble conjugates or the individual beads, respectively.

It is also possible to use different stimuli-responsive polymers in the system. That is, the biomolecule may be conjugated to one polymer and the bead surface may be coated with another, permitting control of their reversible adherence by two different signals. Similarly, the walls or surfaces of the microfluidic device, membrane pores, analytical devices, or other substrates may be coated with a polymer that is different from that which is conjugated to the biomolecule or bead surface, again providing for reversible separation control by two different signals. One can also envisage gradients of polymer composition on surfaces, permitting gradually increasing or decreasing strength of adherence along the length or over the area of the device, depending on the conditions.

The selective separation of polymer-biomolecule conjugates or coated beads by application of a stimulus provides on off control of enzyme reactions, affinity recognition processes, biological or chemical receptor stimulation, and DNA hybridization. The separation can not only be carried out in the channels of a microfluidic device such as a lab on a chip, but it could also be used on the surface of a surface plasmon resonance (SPR) analytical device, biochips, microarrays, chromatography columns, filters, and other diagnostic devices, as well as imaging and therapeutic particle systems.

In another aspect, the invention provides methods for jointly controlling affinity separations and controlled biomolecule activity. The separations step is driven by the reversible formation of polymer-biomolecule or polymer-bead conjugates that gives the nano- or micro-particles different diffusive, sedimentation, and/or adhesive properties. This separation and formation step can be controlled by the molecular orientation of the biomolecules in the nano- or micro-aggregates to be in an active or inactive state, i.e. to be in an on or off state. Upon disaggregation after separation, the free conjugates can go back to their original sizes and diffusive, sedimentation, and/or adhesive properties with their original activities.

In an example of a one embodiment, affinity separations can be applied to microfluidic bioanalytical and diagnostic devices. There are currently three affinity chromatography schemes used for microfluidic systems: (1) direct coating of the channel walls with an affinity moiety; (2) packing a microfluidic channel with affinity-modified particles that are restrained in the column by physical barriers; and (3) filling a column with a monolithic porous slab that is modified with an affinity moiety. These approaches share some disadvantages that have hindered their widespread adoption. While most microfluidic features can be constructed in a single fabrication step (whether fabrication via lithography, polymer molding, or polymer ablation), column construction requires a separate packing or surface modification step. In addition, the packing cannot be changed, and the device can only be used to separate a single target. Similarly, since the affinity column packing is locked in the device at the time of construction, it is difficult or impossible to replenish the activity of a column. This limits the number of times a device can be used and places a strict shelf life on devices containing affinity moieties that are unstable in storage.

The present invention provides a microanalytical system that utilizes stimuli-responsive polymers to create reversibly soluble nanoparticles and larger aggregates that incorporate biomolecules and/or beads. Under standard conditions, the individual stimuli-responsive polymer-conjugates flow through devices as isolated species, but when the polymer associated with the conjugates is stimulated, the conjugates form nanoparticle structures that adhere to the device surfaces or are simply slowly diffusing because of their increased size. This stimuli-responsive behavior is reversible, and the aggregated conjugates can be separated from the device surfaces or disaggregated back to the faster diffusing species by reversing the polymer stimulus.

The invention allows for the packing of affinity chromatography columns at the time of use: the conjugates are flowed into the column and stimulated to aggregate, resulting in a packed column. This feature allows for increased flexibility in microfluidic devices: a single device can be used to separate any number of molecules, depending on how it is packed at the time of use. This flexibility is a boon to device fabrication, because devices no longer have to be packed in a separate step at the time of manufacture. In addition, because column packings can be manufactured and distributed separately from devices, the cost of devices to the end user can be decreased and shelf life issues can be eliminated. Finally, the reversibility of aggregate formation simplifies the elution process: separated biomolecules can be eluted merely by removing the polymer stimulus, eliminating the need for harsh chemical eluents. This technology can be applied to a wide variety of bioanalytical platforms including chromatography columns, filtration devices, and microfluidic lab-on-a-chip, or micro total analysis systems (µTAS).

Stimuli-responsive polymer-conjugates are conjugates of a smart polymer (i.e., stimuli-responsive polymer) and a biomolecule (e.g., a protein, DNA, oligonucleotide [or ODN], peptide, or carbohydrate) that phase separates as an insoluble nanoparticle in a controlled size range when the polymer is stimulated by a small change in conditions such as temperature, pH, or light, and that disaggregates and redissolves when the stimulus is reversed.

In one embodiment, the invention provides a stimuli-responsive polymer-conjugate that includes is a bead (e.g., microbead or particle) that may be (a) coated with a smart polymer, (b) coated with a smart polymer and a biomolecule, as separate entities on the surface, (c) coated with a smart polymer-biomolecule conjugate, and/or (d) coated with a smart polymer and a smart polymer-biomolecule conjugate, as separate entities on the surface. The smart polymer or the smart polymer-biomolecule conjugate may be physically or chemically attached to the bead surface. The bead conjugates also phase separates as an insoluble aggregate when the polymer is stimulated, and disaggregates and redissolves or is re-suspended when the stimulus is reversed.

There are several "actions" that define the various uses of these stimuli-responsive conjugates in bioanalytical and diagnostic technologies.

Figure 3:
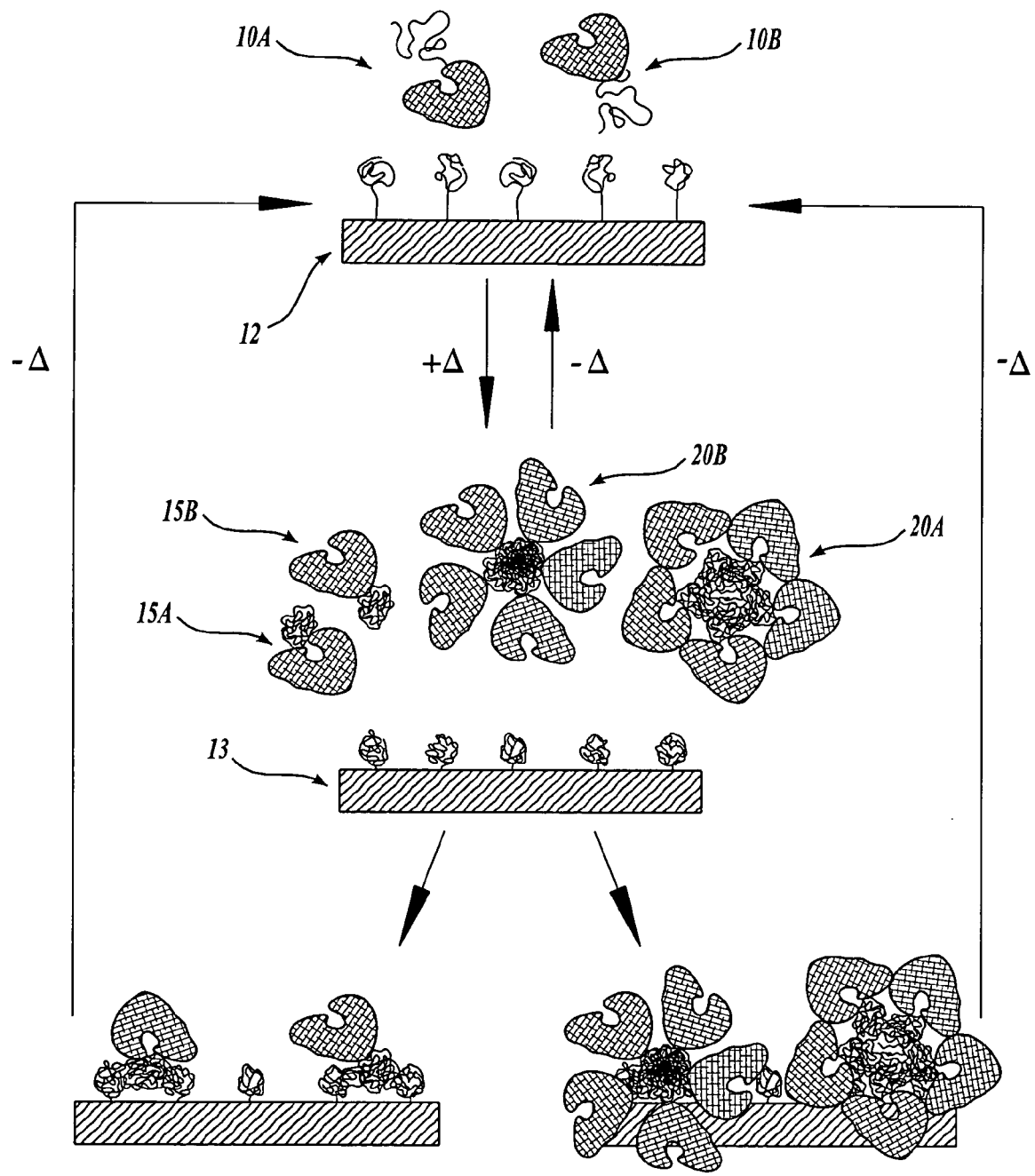
FIG. 3 is an illustration of a representative separation method of the invention in which stimuli-responsive polymer-biomolecule (affinity protein) conjugates (10A and 10B) and their corresponding particles (20A and 20B) are immobilized on a substrate modified to include stimuli-responsive polymers (hydrophobic, associative state, 13); removal of the stimulus dissociates the particle, releasing the particles and conjugates from the substrate (hydrophilic, non-associative state, 12), and regenerates the conjugate in its non-associative state.
Figure 4:
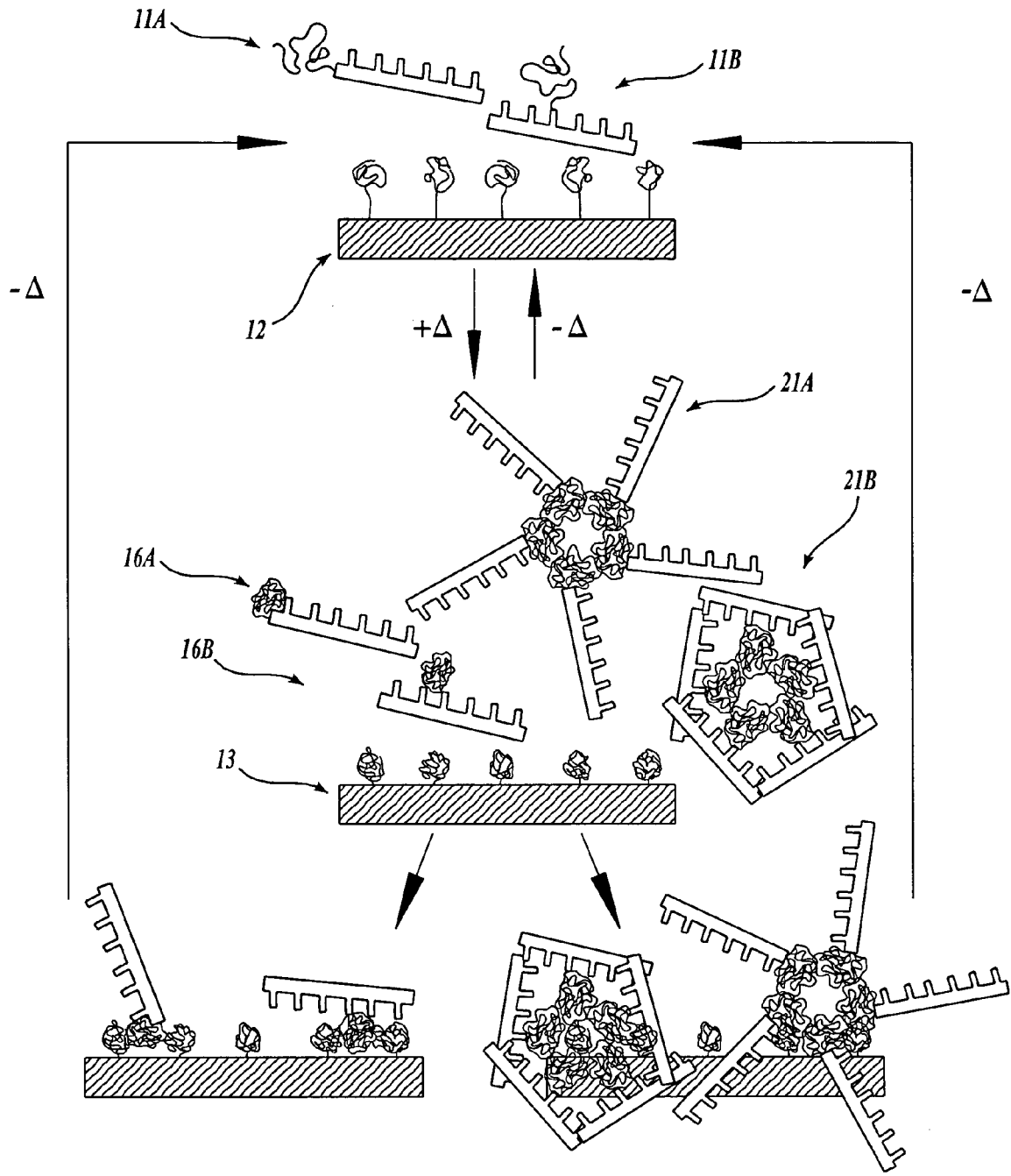
FIG. 4 is an illustration of a representative separation method of the invention in which stimuli-responsive polymer-biomolecule (nucleic acid oligomer) conjugates (11A and 11B) and their corresponding particles (21A and 21B) are immobilized on a substrate modified to include stimuli-responsive polymers (hydrophobic, associative state, 13); removal of the stimulus dissociates the particle, releasing the particles and conjugates from the substrate (hydrophilic, non-associative state, 12), and regenerates the conjugate in its non-associative state.

The first action is to stimulate (by a change in the physical conditions) the polymer component of the conjugates (e.g., nanoconjugates) to phase separate to form individual particles (e.g., nanoparticles). Upon stimulation and by virtue of the polymer component, the conjugate can be rendered more hydrophobic and more adherent to other similar hydrophobic polymers or surfaces. This can lead to formation of individual particles (e.g., nanoparticles) as shown in FIGS. 1A, 1B, 2A, and 2B, and further cause them to adhere to the hydrophobic surfaces of beads or to other surfaces of a device or component of analytical or separation systems, such as surfaces of porous particles, membranes, biochips, microarrays, microfluidic channels, or other surfaces of devices. FIGS. 3 and 4 illustrate the interaction of stimuli-responsive polymer conjugates and their respective aggregates with stimuli-responsive polymer modified surfaces. FIG. 3 illustrates protein conjugates and FIG. 4 illustrates nucleic acid conjugates. As shown in the figures, all of these actions may be reversed by reversing the stimulus.

In a similar manner, simple coatings of the stimuli-responsive polymers onto beads or other surfaces of a device or component of an analytical or separation system as described above may be stimulated to become hydrophobic, and mutually adherent, as shown in FIG. 5. Referring to FIG. 5, in the absence of stimulus, beads and substrate surfaces modified to include stimuli-responsive polymers are hydrophilic and not associated; upon stimulus (+Δ), the polymers become hydrophobic and associative, which, depending on the situation, can result in the association of the polymer-modified bead to the polymer-modified surface or the association of a plurality of polymer-modified beads to form aggregates; upon the removal of the stimulus (−Δ), the polymers return to their hydrophilic state and are not associative.

For the aggregates described above, including nanoparticle aggregates and micron-scale bead particles, these particles will diffuse and/or sediment at different rates from their individual components in solution (e.g., polymer-biomolecule conjugates or nanoconjugates) or in suspension (individual beads). This can permit local isolation and separation of the hydrophobic aggregates by diffusion or sedimentation, such as in microchannels in fluidic devices.

Referring to FIGS. 1A, 1B, 2A, and 2B, depending on the specific site where the polymer is conjugated to the biomolecule (e.g., protein in FIGS. 1A and 1B, and nucleic acid in FIGS. 2A and 2B), the stimulus can cause the polymer to block the recognition capability of the biomolecule. Thus, the application of a stimulus can not only cause the physical separation of a conjugate, it may also cause its biological inactivation. This action is reversible, when the stimulus is reversed.

Figure 6:
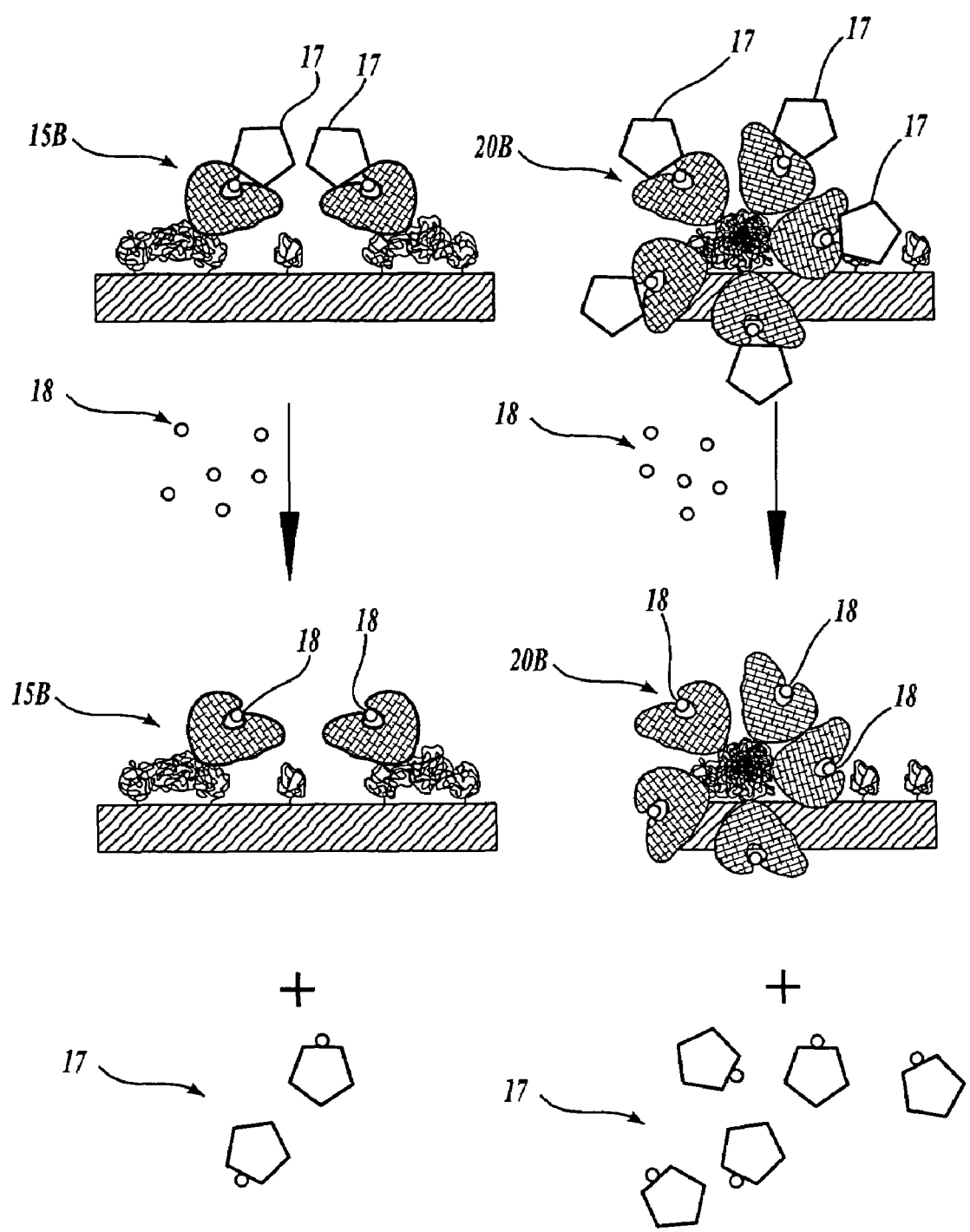
FIG. 6 illustrates the use of conjugates (15A) and representative particles of the invention comprising a plurality of conjugates (20A) to effect affinity ligand separation; competitive binding ligand (18) is applied to immobilized conjugates (15A) and particles (20A) with bound target compound (17) displacing bound target compound (17) to provide immobilized conjugates (15A) and particles (20A) with bound ligand (18) and released target compound (17)

It is also possible to isolate and recover a molecule that has bound by affinity to the protein in the conjugate (e.g. nanoconjugate), by utilizing the actions described above to isolate the particles (e.g., nanoparticles) containing the affinity bound ligand, and then eluting off the ligand by addition of a competing small ligand (such as a peptide that releases a bound protein). FIG. 6 shows this action. Referring to FIG. 6, target compounds (e.g., affinity ligands) are shown bound to their affinity proteins (e.g., target binding partners). As shown in the figure, affinity proteins are coupled to stimuli-responsive polymers to form stimuli-responsive polymer-biomolecule (i.e., affinity protein) conjugates. In these figures, the conjugates are associated with a substrate that has been modified to include a stimuli-responsive polymer. FIG. 6 shows the conjugate with bound target compound associated the substrate and a particle comprising a plurality of conjugates with bound target compound associated with the substrate. The binding of the affinity ligand to the polymer-affinity protein conjugate provides localization/sequestration/immobilization of the ligand on the surface of the substrate (e.g., bead or channel wall). The target compound can be released from the immobilized conjugate by displacement with a second affinity ligand. This process permits the selective removal of the affinity ligand for the purpose of reaction, recovery, analysis, or disposal depending on the particular system.

Physical conditions such as pH and ionic strength may also be modified to cause the release and permit recovery of the bound ligand, similar to techniques used in chromatographic separation systems. One can envisage a similar method to recover the complementary sequence of a single stranded DNA bound to a polymer-DNA nanoparticle. Dye molecules may be conjugated to the bound ligands, or other imaging techniques may be applied to identify the presence of the bound biorecognition molecules, permitting image analysis to assay their presence and concentration.

Figure 7A:
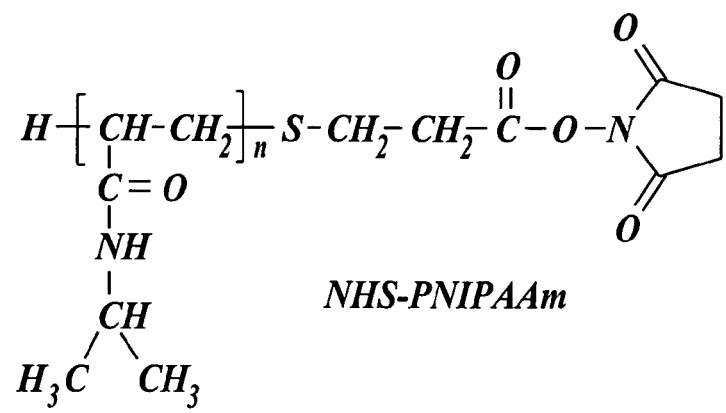
FIGS. 7A and 7B illustrate the chemical structures of bead modification agents.
Figure 7B:
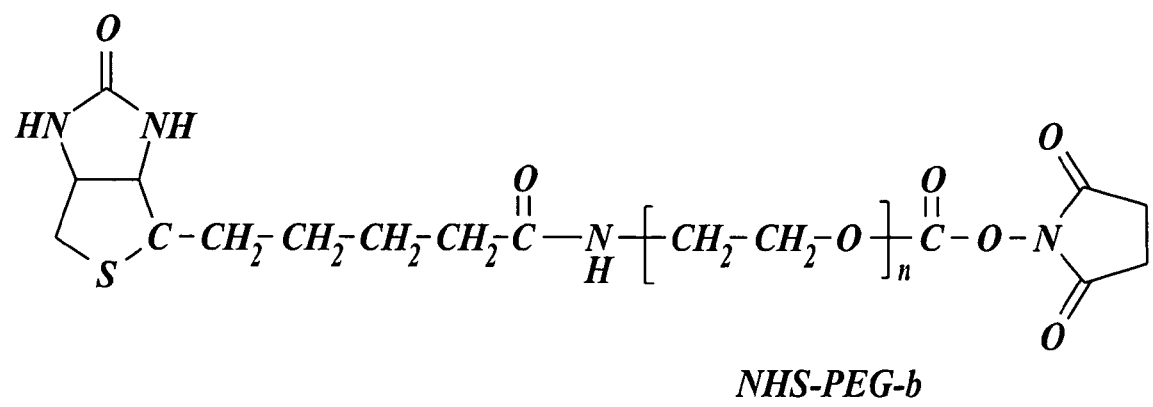
Figure 8:
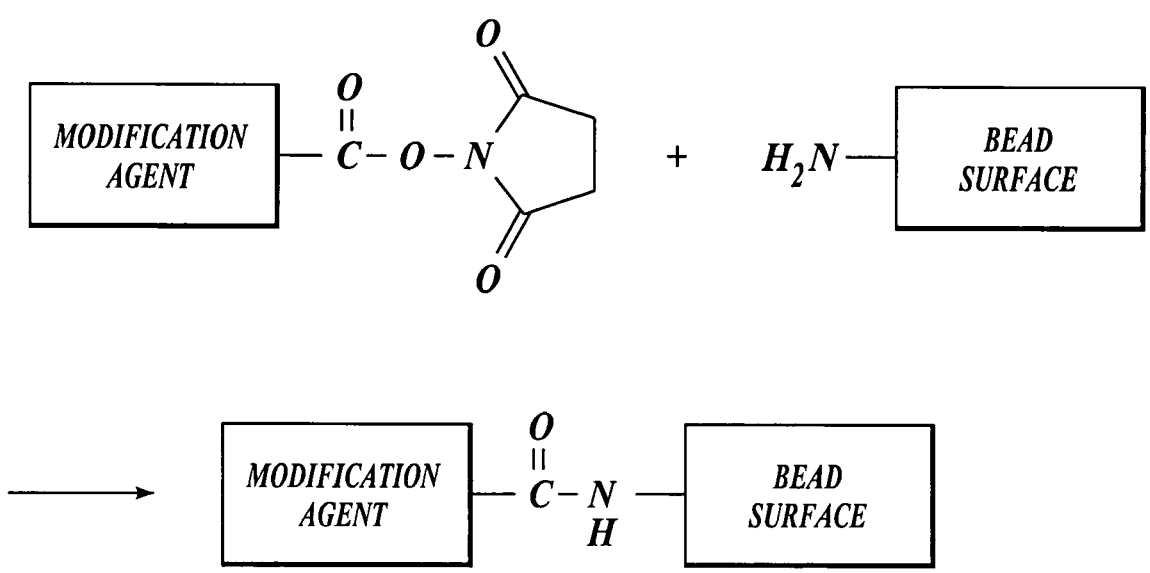
FIG. 8 illustrates a representative bead modification reaction of a primary amine with an NHS-ester.

The processes described above represent one embodiment of the methods of the invention that include stimuli-responsive polymer-bead conjugates. It will be appreciated that other formats are possible. One representative format in which modified beads as useful as a chromatographic matrix suspension is described below. For example, latex beads having diameters of 100 nm and coated with primary amine groups, are covalently modified with 11 kDa poly(N-isopropylacrylamide) (PNIPAAm), a representative temperature sensitive polymer, and 3.4 kDa poly(ethylene glycol)-biotin (PEG-biotin or PEG-b) by N-hydroxysuccinimide (NHS) ester conjugation chemistry. Formulas for the modification agents are given in FIG. 7, and the chemical reaction facilitating covalent modification is shown in FIG. 8. This modification includes two steps. Initially, beads are modified with PEG-biotin by reaction with an NHS ester of PEG-biotin (NHS-PEG-b) at a 1:10 molar ratio of surface amine groups to NHS-PEG-b. The reaction is performed in aqueous conditions at pH 9.0 and 4° C., and is allowed to proceed overnight. This molar ratio and reaction conditions have been shown to result in modification of about 40% of the available amine groups on the bead surfaces. The PEG-b modified beads are separated from unreacted NHS-PEG-b by threefold centrifugation and resuspension.

The second modification step includes the reaction of PEG-b modified beads with an NHS ester of PNIPAAm (NHS-PNIPAAm). The reaction is performed at a 10-fold molar excess of NHS-PNIPAAm relative to unmodified surface amine groups (assuming 40% modification of surface amines in the first step). This reaction is also performed in aqueous conditions at pH 9.0 and 4° C., and is allowed to proceed overnight. The doubly modified beads are separated from unreacted NHS-PNIPAAm by threefold centrifugation and resuspension; this centrifugation is performed at 4° C. to avoid phase transition and aggregation of unreacted NHS-PNIPAAm.

Figure 9A:
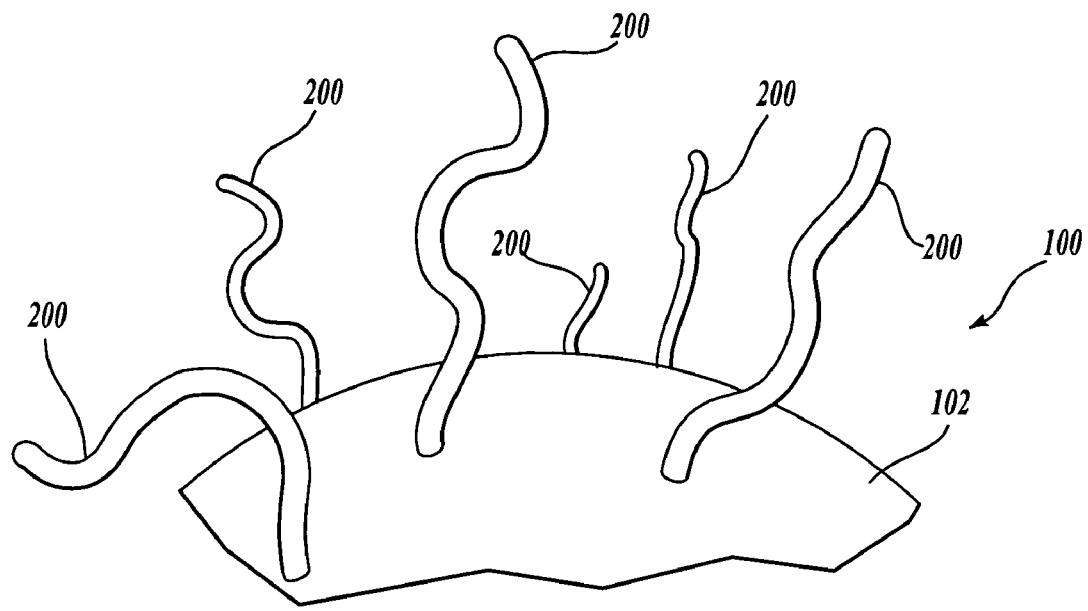
FIGS. 9A and 9B are illustration of representative singly- and doubly-modified beads of the invention, (100) and (104), respectively.
Figure 9B:
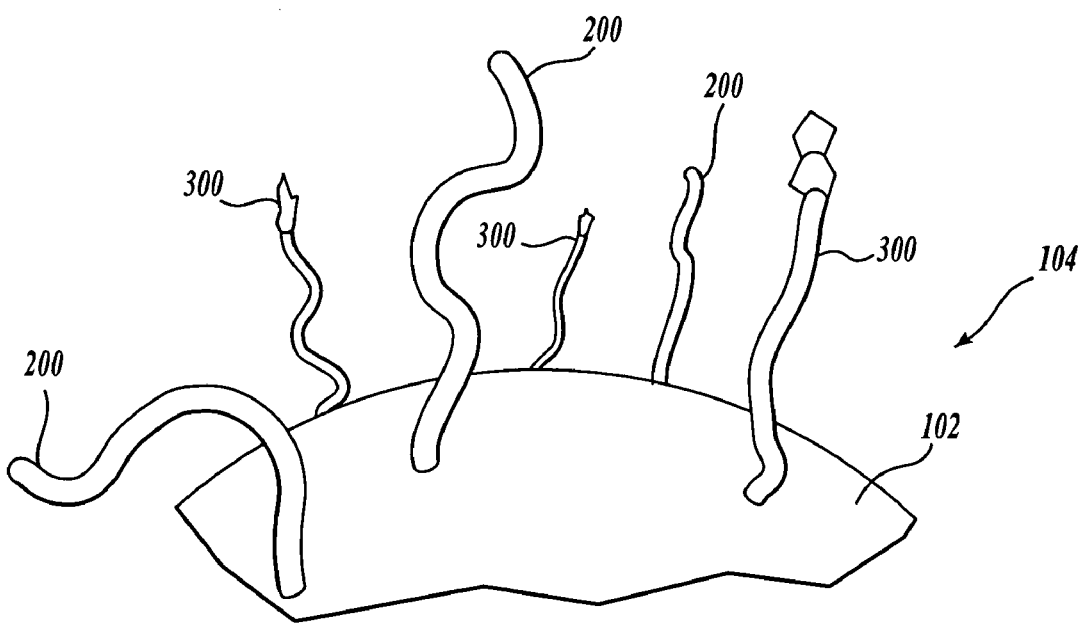

In addition to the doubly modified PEG-b/PNIPAAm beads, singly modified PNIPAAm beads are prepared. The protocol for PNIPAAm modification is identical to that given above for the second step of the dual modification process, maintaining the tenfold excess of NHS-PNIPAAm over free amines in the reaction. FIG. 9 is a schematic rendering of both types of beads. FIG. 9A illustrates a portion of the surface of a singly modified bead (100) having bead surface (102) with attached PNIPAAm (200). FIG. 9B illustrates a portion of the surface of a doubly modified bead (104) having bead surface (102) with attached PNIPAAm (200) and attached PEG-b (300).

The modified beads are one component of the chromatographic matrix suspension. To complete this suspension, dual-modified PEG-b/PNIPAAm beads are mixed with singly-modified PNIPAAm beads, a solution of 11 kDa PNIPAAm, and pH 7.6 phosphate buffered saline (PBS) to final concentrations of 0.6 wt % latex (from beads), 1.67 mg/mL PNIPAAm, 50 mM phosphate, and 5 mM sodium chloride. PEG-b/PNIPAAm beads contribute half of the latex in this suspension; the other half comes from PNIPAAM beads. The suspension is degassed by agitation under vacuum for approximately five minutes.

Figure 10:
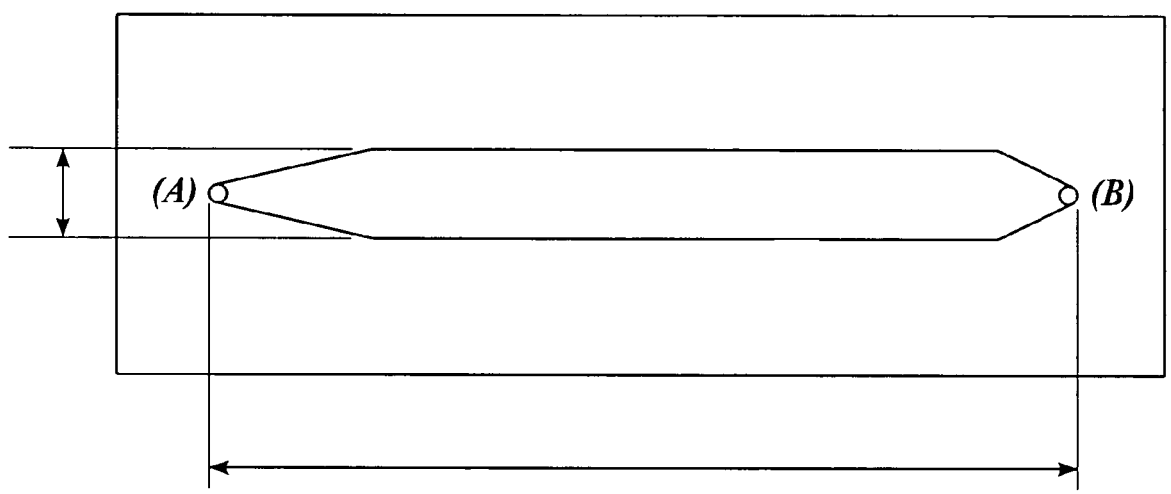
FIG. 10 is a top view of representative microfluidic device useful in practicing a method of the invention.
Figure 11:
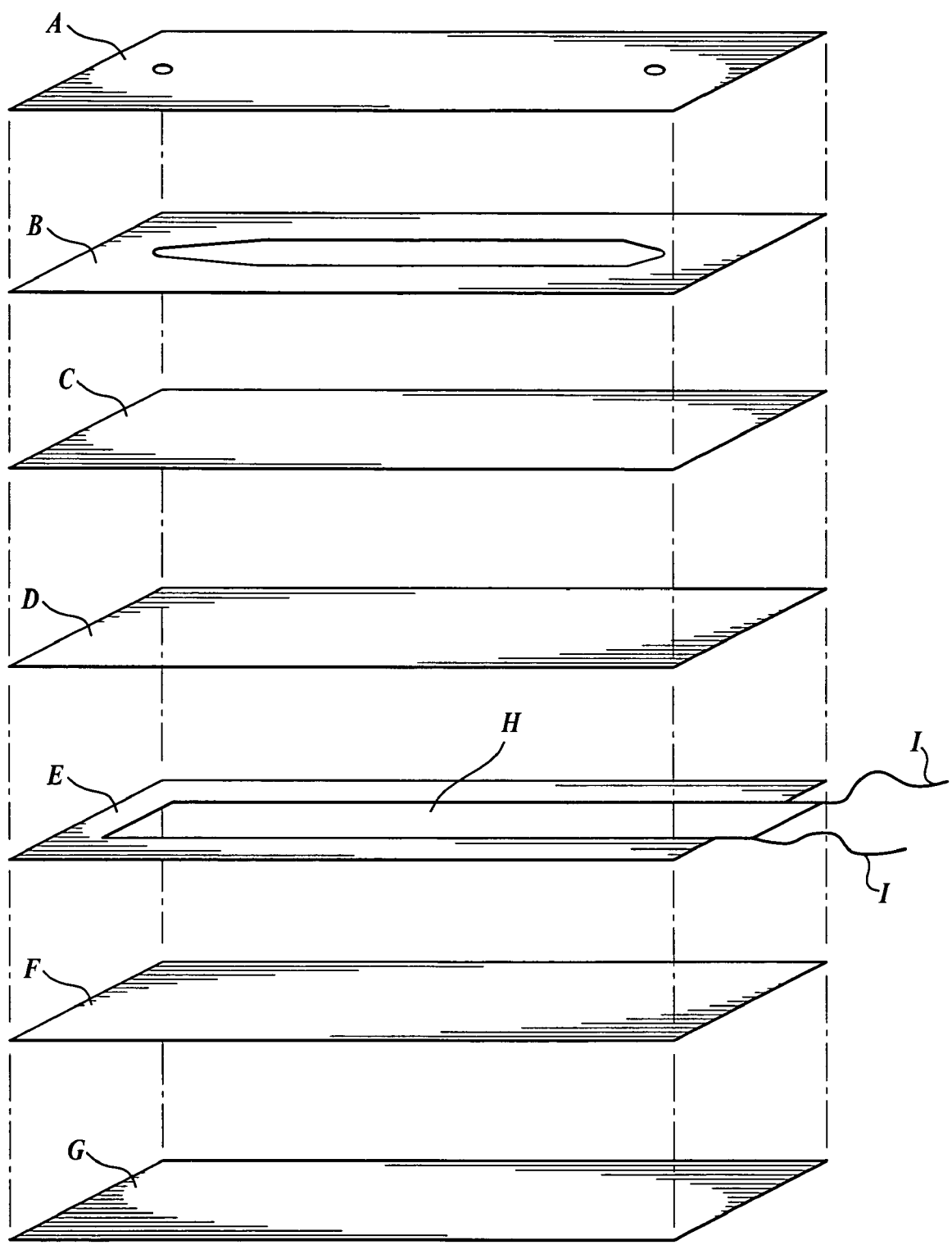
FIG. 11 is an exploded view of the device of FIG. 10.

Initial demonstrations of the matrix were carried out in a microfluidic device as shown schematically in FIGS. 10 and 11, although the invention will function in a wide variety of chromatography and filtration devices and channels. The demonstration device was constructed from stacked poly(ethylene terephthalate) (PET) sheets. Two-dimensional features were cut into these sheets via ultraviolet (UV) laser ablation and the cut sheets were stacked and joined with adhesive to form three-dimensional features. FIG. 10 is a top view of the device, showing the channel, the inlet port (A), and the outlet port (B). In a representative embodiment, the channel has dimensions 40 mm×4 mm×100 µm. FIG. 11 is an exploded view of the device, showing the PET layers from which it is constructed: (A) a 100 µm-thick layer containing the input and output ports; (B) a 100 µm-thick layer containing the channel features and coated on both sides with adhesive; (C) a 100 µm-thick layer sealing off the channel; (D) a 100 µm-thick layer coated on both sides with adhesive; (E) a 300 µm-thick layer containing the heater; (F) a 100 µm-thick layer coated on both sides with adhesive; and (G) a 100 µm-thick layer. Also shown in FIG. 11 are (H) a thin-film resistive heater and (I) the electrical leads connected to this heater.

Affinity chromatography using the materials and methods of the invention was demonstrated using the avidin:biotin system. In this system, streptavidin is the target compound and biotin is the target binding partner/affinity ligand). Three-hundred microliters of the matrix suspension are manually injected into the channel of the demonstration device, using a 1 mL syringe directly connected to the device input line. The device input line is then connected to a 1.5 mL sample loop, which has been previously been loaded with a sample sequence. This sequence consists of 100 µL PBS, to serve as a column wash; 150 µL fluorescently-labeled streptavidin solution at a concentration of 2.5 µM, the biotin binding species; and 1250 µL PBS, to wash through excess streptavidin and to serve as the elution buffer. After connecting the device input to the sample loop, the device heater is activated, bringing the fluid in the channel to a temperature of 45° C. and leading to the phase transition and surface adhesion of the matrix suspension.

With the matrix formed in the channel, the contents of the sample loop are pushed through at a rate of 10 µL/min using a syringe pump. The fluid that flows through the system is collected at the device output line in 50 µL aliquots. The initial wash buffer in the sample loop flows through the system first, bringing with it any beads that have not been bound to the channel walls. Next, the streptavidin sample flows through the channel and is bound to the biotin-modified beads. Any unbound streptavidin exits the system and is collected. Once the entire streptavidin sample has passed through the channel, the heater is deactivated, reducing the channel temperature and causing the chromatographic matrix to dissociate from the channel walls. This dissociated matrix, bound to captured streptavidin molecules, flows through the channel with the final buffer wash and is collected at the output.

The methods of the invention can also be applied to molecular separations technology that also incorporates control of biomolecular recognition that regulates protein and DNA activity. This technology for the reversible control of separations and activity is applicable to a wide variety of specific bioanalytical and diagnostic technology. The general applications include: (1) reversible control of affinity separation capture and release steps, for example, when and where a target protein, cell, DNA species, metabolite, reaction product, toxin, is separated and then released for collection for subsequent analytical steps, or for disposal; and (2) reversible control of affinity protein, enzyme, and DNA hybridization activities by sequestration of their active sites in nano- and micro-particles of stimuli-responsive polymer-biomolecule and/or stimuli-responsive polymer-bead conjugates Examples of specific applications include: (1) purification of a target protein or DNA species from a complex fluid such as blood in a microfluidic channel for subsequent analysis by PCR or immunoassay; (2) isolation of target bacterial pathogens for environmental sensing in the food industry or military by using a simple membrane filter device; (3) purification of activated dendritic cells in complex tissue samples for subsequent use in therapeutic vaccine formulation; and (4) control of enzyme activities in lab-on-a-chip microfluidic channels where the enzymes are kept off during flow until they enter a reaction chamber where they are spatially and temporally turned on at the right time.

In the representative microfluidic device and method described above, the purification of a biochemical species is exemplified. Because biochemical affinity interactions are extremely specific, only molecules specific for the affinity moiety (i.e., target binding partner) on the beads will bind to the chromatographic matrix that is adhered to the channel surface; other molecules will pass through with the wash. The specifically bound molecule can then be eluted by decreasing the temperature (when temperature responsive polymers are used) in the channel and dissociating the matrix. In the particular implementation described above, streptavidin is specifically bound by the affinity chromatography matrix, and the eluted matrix will contain pure streptavidin and the biotinylated bead separated from any contaminants present in the initial sample.

Another example is the concentration of specific biochemical species. The chromatographic matrix is stable in flow, but easily reversible upon a reduction in temperature. It is therefore possible to pass a low-concentration sample of an affinity biomolecule over the matrix, allowing this molecule to bind to the matrix, over a relatively long time scale. Then, over a much shorter time scale, the temperature of the matrix can be reduced and the bound biomolecule eluted from the system. The resulting product stream will contain a higher concentration of the target biomolecule than the input stream. Concentration processes are important both in schemes for production of biomolecules, in which the product is desired at the highest possible concentration, and in analytical assays for the presence of specific biochemicals, which are limited to detecting their targets at concentrations above some minimum threshold concentration. This method of the invention could therefore contribute to general biochemical analytical assays by increasing the concentration of dilute input samples.

The materials and methods of the invention include modifications of those described herein. For example, the bead size and material can be varied. Bead size is limited on the lower end by technologies for manufacturing surface-active beads; it is limited on the upper end by bead sizes that would sediment rapidly. In addition to latex, suitable beads may be made of polystyrene, silicone, glass, agarose, or other materials. The ratio of affinity moiety (i.e., target binding partner) to stimuli-responsive polymer on the bead surface can be varied from the 2:3 ratio used in the above example. The size of both the affinity moiety tether (3.4 kDa PEG) and polymer can also be varied. In addition, the method of bead modification is not limited to covalent attachment by NHS ester chemistry. Modified beads can have other covalent links, such as disulfide bonds, or noncovalent links such as electrostatic interactions, oligonucleotide complementarity, or streptavidin-biotin binding. Potential modification techniques include the addition of labile links to facilitate the cleavage of affinity moieties or smart polymers from the bead surface.

Similarly, the contents of the matrix suspension may be varied from that described above. The suspension need not contain free polymer or singly modified beads, but if it does, it need not contain them at the concentrations given above.

Variation of the concentrations of these components may be necessary to optimize performance in a particular microfluidic device. In addition, the free polymer added to the matrix suspension need not be the same as the polymer attached to the surface of the beads; it can have a different size or chemical composition. The materials and methods of the invention are generally applicable to microfluidic separation and concentration systems.

One key to the flexibility and utility of the materials and methods of the invention is that a wide variety of affinity moieties (i.e., target binding partners) can be attached to the beads to bind a wide variety of biomolecules (i.e., target compounds). The example described above can be trivially modified to bind other affinity targets by using streptavidin molecules to connect the biotin moieties on the surface of the beads to a biotinylated version of the desired affinity moiety. It is also possible, however, to connect the desired affinity moiety directly to the beads' surfaces or to a tether on the beads' surfaces, with no intervening biotin-streptavidin linkage. A variety of affinity interactions have been employed in affinity chromatography systems. Primary among these are immunological (antibody/antigen) interactions and specific protein-protein interactions. Similarly, enzymes have been purified by affinity to substrate analogs, and specific oligonucleotides have been purified by sequence complimentarity. Aside from these molecule-specific interactions, a number of techniques relying on affinity tags have been developed. In these schemes, a target biomolecule is labeled, either chemically or via recombinant protein engineering, with a specific chemical moiety. The chromatographic matrix contains an affinity ligand with which this moiety associates. The most prominent example of this approach is metal affinity chromatography, in which target molecules are labeled with polyhistidine tags. These tags interact with divalent metal cations such as $Ni^{2+}$, $Cu^{2+}$, or $Zn^{2+}$, which are chelated to the matrix. Another emerging technology involves tagging the target molecule with biotin and separating it by (strept)avidin affinity chromatography. The materials and methods of the invention can employ any of these affinity interactions to separate or concentrate biomolecules.

Additional flexibility can be introduced to the system by varying the stimuli-responsive polymer. Smart polymers that respond not to temperature, but to pH, ionic strength, specific wavelengths of light, or other environmental stimuli are available. Any of these polymers can be used to build a stimuli-responsive chromatography matrix. In addition, if beads are modified with specific affinity moiety/stimuli-responsive polymer pairs, an individual stimulus becomes associated with a specific affinity molecule. In other words, all beads that bind an exemplary biomolecule A respond to one stimulus, and all beads that bind exemplary biomolecule B respond to a different stimulus. It is then possible to use a mixture of beads to capture several specific species of biomolecules from a complex mixture and elute them separately according to their associated stimuli, allowing for simultaneous separation or concentration of several species.

In addition to the basic separation and concentration applications described above, the materials and methods of the invention can be used to manipulate biochemicals in a variety of bioanalytical and diagnostic devices. In one application, a biomolecule of interest is pre-bound to stimuli-responsive polymer beads. As this bead/biomolecule complex flows through a device, it enters a region where the stimuli-responsive polymer phase transition can be induced. If this transition is induced, the beads will stick to the sides of the channel, taking the pre-bound biomolecule of interest with them. Phase transition can be reversed later, releasing the beads and bound biomolecule. In this mode of operation, the invention provides a biochemically specific microfluidic valve, allowing or blocking specific biomolecules from entering a region of a microfluidic device according to a stimuli-responsive polymer stimulus, which is controlled by the device operator. Of course, several different stimuli could be associated with several different biomolecules, allowing for a valve system that controls the entry of several different species of biomolecules. This application allows for microfluidic devices that operate upon several different biomolecules in the input stream; by incorporating chemically specific valves in a device, the distribution of the biomolecules can be controlled, and they can be delivered to the appropriate region of a device at the appropriate time.

In another embodiment, the materials and methods of the invention can also be used in immunoassay. In such an assay, the beads are modified with an antibody or antigen and immobilized on the wall of a microfluidic channel or other bioanalytical device (e.g. chromatography column, filtration device). A sample is passed through the channel, and any molecules (i.e., target compound) that bind the immobilized agent stick to the wall of the channel. Next, a fluorescently labeled molecule (i.e., indicator or reporting agent), also capable binding the target, is flowed through the channel. The indicator binds any target compound in the channel; the amount that binds is proportional to the amount of target present. The fluorescent signal of the indicator is then detected, either by directly probing the channel or by releasing the immobilized beads and analyzing the fluid leaving the device, to determine the presence and concentration of the target compound in the sample. This scheme is superior to current immobilized-phase microfluidic immunoassays because the invention can be reversibly immobilized, allowing for one device to be used for several assays: potentially even assays for different molecules. The immobilized phase can be easily renewed by eliminating the stimuli-responsive polymer stimulus, injecting a new matrix suspension, and reintroducing the stimulus.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A device, comprising a surface and a conjugate,
    the surface comprising a first polymer covalently coupled to the surface, wherein the first polymer is reversibly associative in response to a stimulus;
    the conjugate comprising a second polymer, wherein the second polymer is reversibly associative in response to the stimulus;
    wherein the conjugate is immobilized on the surface only through an associative interaction between the first and second polymers; and
    wherein the stimulus is a temperature-sensitive stimulus and the first and second polymers are independently selected from the group consisting of a poly(N-isopropylacrylamide) and a copolymer of N-isopropylacrylamide.

2. The device of claim 1, wherein the surface is a surface of at least one of a microfluidic channel, a membrane, a biochip, a microassay, a bead, or a filter.

3. The device of claim 1, wherein the conjugate is a polymer-biomolecule conjugate.

4. The device of claim 3, wherein the biomolecule is a protein or a peptide.

5. The device of claim 1, wherein the first polymer is the same as the second polymer.

6. The device of claim 3, wherein the conjugate further comprises a target binding partner, wherein the target binding partner forms a biorecognition interaction with a target compound.

7. The device of claim 6, wherein the target binding partner is an affinity protein or peptide.

8. The device of claim 6, wherein the target compound is an affinity ligand.

9. The device of claim 6, wherein the target compound is an antibody and the target binding partner is an antigen.

10. The device of claim 6, wherein the target compound is an antigen and the target binding partner is an antibody.

11. The device of claim 6, wherein the target compound is a protein or peptide and the target binding partner is a protein or peptide.

12. A device, comprising a surface and a conjugate, the surface comprising a first polymer covalently coupled to the surface, wherein the first polymer is reversibly self-associative in response to a stimulus;

the conjugate comprising a second polymer, wherein the second polymer is reversibly associative in response to the stimulus;

wherein the conjugate is immobilized on the surface only through an associative interaction between the first and second polymers; and wherein the stimulus is a temperature-sensitive stimulus and the first and second polymers are independently selected from the group consisting of poly(N-isopropylacrylamide) and a copolymer of N-isopropylacrylamide.

* * * * *

UNITED STATES PATENT AND TRADEMARK OFFICE
CERTIFICATE OF CORRECTION

PATENT NO. : 7,625,764 B2 Page 1 of 1
APPLICATION NO. : 11/197771
DATED : December 1, 2009
INVENTOR(S) : P. S. Stayton et al.

It is certified that error appears in the above-identified patent and that said Letters Patent is hereby corrected as shown below:

| COLUMN | LINE | | |
|---|---|---|---|
| 26 | 6 | "associative" should read | |
| (Claim 12, | line 6) | --self-associative-- | |

Signed and Sealed this

Thirteenth Day of April, 2010

David J. Kappos
*Director of the United States Patent and Trademark Office*